United States Patent
Grage et al.

(10) Patent No.: US 11,517,019 B2
(45) Date of Patent: Dec. 6, 2022

(54) MICROBICIDAL SYSTEM

(71) Applicant: ABLELIFE BIOTECH, Inc., Atlanta, GA (US)

(72) Inventors: Henry M. Grage, Johns Creek, GA (US); Arthur S. Freeman, Dallas, TX (US)

(73) Assignee: About Better Life Experiences, LLC, Atlanta, GA (US)

( * ) Notice: Subject to any disclaimer, the term of this patent is extended or adjusted under 35 U.S.C. 154(b) by 0 days.

(21) Appl. No.: 17/172,058

(22) Filed: Feb. 9, 2021

(65) Prior Publication Data

US 2021/0307330 A1    Oct. 7, 2021

Related U.S. Application Data

(60) Provisional application No. 63/003,801, filed on Apr. 1, 2020.

(51) Int. Cl.
*A01N 47/44* (2006.01)
*B01D 46/00* (2022.01)
*A61L 9/012* (2006.01)
*B01D 69/14* (2006.01)

(52) U.S. Cl.
CPC ......... *A01N 47/44* (2013.01); *B01D 46/0028* (2013.01); *B01D 2257/91* (2013.01); *B01D 2258/06* (2013.01); *B01D 2311/2692* (2013.01)

(58) Field of Classification Search
CPC .. A01N 47/44; B01D 46/0028; B01D 69/141; A61L 9/012
See application file for complete search history.

(56) References Cited

U.S. PATENT DOCUMENTS

| | | | |
|---|---|---|---|
| 7,427,409 B2 | 9/2008 | Gooch et al. |
| 2007/0218522 A1 | 9/2007 | McCoy |
| 2008/0272062 A1 | 11/2008 | Gooch |
| 2008/0306301 A1 | 12/2008 | Gooch et al. |
| 2009/0191250 A1 | 7/2009 | Gooch et al. |
| 2010/0125105 A1 | 5/2010 | Gooch et al. |
| 2011/0086078 A1 | 4/2011 | Gooch et al. |
| 2016/0251571 A1 | 9/2016 | Agrawal et al. |
| 2016/0360745 A1 | 12/2016 | Johnston et al. |
| 2018/0064604 A1 | 3/2018 | Drmanovic |
| 2019/0077747 A1 | 3/2019 | Cattel et al. |

FOREIGN PATENT DOCUMENTS

EP    0 735 852 A1    10/1996

*Primary Examiner* — Kevin Joyner
(74) *Attorney, Agent, or Firm* — F. Russell Denton; Denton Intellectual Property Law Firm, LLC

(57) ABSTRACT

The invention provides a system for sanitizing fluids such as water and air. In particular, the invention provides a combination of solid chlorhexidine and a polymer matrix, for which effluents are essentially free of leached chlorhexidine. The systems enable rapid disinfecting of fluids, including in line at the point of use, and can be employed for both high volume applications and disposable single-use applications.

20 Claims, 9 Drawing Sheets
(3 of 9 Drawing Sheet(s) Filed in Color)

MICROBICIDAL SYSTEM

BACKGROUND OF THE INVENTION

Field of the Invention

This invention relates to microbicidal systems and their use to purify fluids.

State of the Technology

Pathogenic contaminants pose an ongoing challenge for public health, particularly in water and air. The Legionnaires' disease organism illustrates the problem. *Legionella pneumophila* serogroup 1 (Lp1) is a bacterium found naturally in freshwater lakes and streams. When it finds its way into water systems in buildings, it can proliferate in showerheads and sink faucets, cooling towers, poorly managed hot tubs, decorative fountains, hot water heaters and tanks, and large plumbing systems. Lp1 can survive at temperatures up to ~145° F. (60° C.). If the water is dispersed in fine droplets in mists or showers, it can be inhaled, just as it can be inhaled from contaminated air. Lp1 is pernicious in persons with weakened lungs, such as: current and ex-smokers; cancer and lung disease patients; patients 50 years of age or older; and patients with diabetes, kidney disease, or liver disease. In fact, Lp1 infects far more effectively by transfer in contaminated water than from person to person. Lp1 causes Legionnaire's disease or sometimes flu-like Pontiac fever; 10,000 cases of Legionnaire's disease are diagnosed annually in the U.S. but it is infrequently tested for, thus badly underdiagnosed. One tenth of known Legionnaire's patients die from the condition. Other airborne diseases are better known but similarly problematic, for pathogens ranging from flu and cold viruses to coronavirus.

The obvious solution is to disinfect the media by which these pathogens infect humans. However, both water and air are commodities, meaning that they are inexpensive and used in large quantities. Consequently, their purification must be fast, reliable, effective, convenient, and cost-competitive with the existing technologies. For instance, to find wide use the technology must be essentially fail-proof for long periods under a wide variety of operating conditions. And the maintenance, replacement and downtime must be kept to a minimum.

Applications for water purification range from potable drinking water to fermentation media and separation of components in biological fluids. The latter two are especially sensitive to microbial contaminants. Applications for air purification include (re)circulated air in homes, offices, hospitals, clean rooms, air- and spacecraft. HEPA filters are popular to remove microbial particulates such as dust, mold, and allergens from air.

Existing water- and air purification methods are diverse, including distillation, reverse osmosis, ion-exchange, chemical adsorption, coagulation and filtering or retention (physical occlusion of particulates). Chemical methods include the use of reagents to oxidize, flocculate or precipitate impurities. The range of particle size exclusion depends on the size of pores or interstitial spaces in membranes and granular materials, respectively. Other methods use purification materials that react chemically with contaminants. Generally, complete purification requires a plurality of complementary techniques, so it is common to employ several devices in series, each with a different function. Examples include mixed resins to remove negatively and positively charged species as well as charge-neutral species.

However, processing and apparatus costs limit the scope of economically viable applications. And the thriftiest techniques have been insufficiently effective against microbial contaminants such as bacteria and viruses. Membranes to remove cell-sized particulates are still somewhat pricey, yet the alternative is to use potent chemicals such as bleach, chlorine, ozone, and the like.

The Environmental Protection Agency (EPA) regulates water sanitation devices. It requires that purification leave essentially no chemical trace in water, and that the microbial content be virtually eliminated. This includes at least a 6-log reduction (99.9999%) in common coliforms, represented by the bacteria *E. coli* and *Klebsiella terrigena*, for samples in which they are present initially at $1 \times 10^7$ (cells)/100 mL. For claimed removal of common viruses, as represented by process-resistant poliovirus 1 (LSc) and rotavirus (Wa or SA-11), the EPA requires a 4-log reduction, 99.99% of cells, from an $1 \times 10^7$ (cells)/L influent. Another challenge is protozoa, which commonly exist in cysts and cause diarrhea, as represented by *Giardia muris* or *Giardia lamblia*. Protozoa are widespread, difficult to treat medically, and resist chemical disinfection. The EPA's minimum standard there is a 3-log reduction, 99.9% of cysts removed, from $1 \times 10^6$ (cells)/L or $1 \times 10^7$ (cells)/L influent. The EPA has allowed the use of inanimate particles of comparable size as a stand-in for disease cells when testing devices.

The EPA has not established comparable standards for Lp1 control, but estimates that current municipal water purification provides a 3-log (99.9%) reduction in Legionella bacteria before it enters buildings. Seemingly Lp1 colonizes and proliferates there afterward.

Certain work on water purification has focused on chlorhexidine and its derivatives to eliminate microbes. Examples follow.

U.S. Pat. Pub. No. 2007-0218522 (McCoy) discloses use of chlorhexidine to kill *Legionella* and other heterotrophic aerobic bacteria collected from plumbing and water supplies, for the purpose of counting them.

U.S. Pat. Pub. No. 2008-0272062 (Gooch et al, Nov. 6, 2008) discloses a pass-through fluid treatment device within which is secured a broad-spectrum antimicrobial material such as a biguanide hydrate such as chlorhexidine hydrate.

U.S. Pat. Pub. No. 2008-0306301 (Gooch et al., Dec. 11, 2008) discloses a composition for treating water, air and other fluids. It includes a biguanide dihydrate compound, such as a hydrate of chlorhexidine, with broad spectrum antimicrobial activity.

U.S. Pat. Pub. No. 2009-0191250 (Gooch et al., Jul. 30, 2009) discloses composite materials with broad spectrum antimicrobial properties for fluid treatment. The materials may include combinations of activated carbon and with particles of chlorhexidine hydrate, useful in fixed particle bed water treatment devices and methods.

U.S. Pat. Pub. No. 2010-0125105 (Gooch, May 20, 2010) discloses fibers and particulates comprising a thermoplastic polyolefin into which is blended 1-25 weight % antimicrobial bisguanide compound such as chlorhexidine. These materials are secured in a pass-through housing through which water may be flowed for antimicrobial purification.

U.S. Pat. Pub. No. 2011-0086078 (Gooch et al., Apr. 14, 2011) discloses fibrous antimicrobial materials for uses including water filtration. The materials are prepared from miscibly blended solids of bisguanides such as chlorhexidine with thermoplastic polymers, e.g. polyolefins. The materials are useful as extruded fibers or in the particulate form for preparing nonwoven materials. Methods for formation and use are also taught.

U.S. Pat. No. 7,427,409 (Gooch et al., Sep. 23, 2008) discloses broad spectrum antimicrobial materials for fluid treatment, where the materials include biguanide hydrates and bases, in particular a hydrate of chlorhexidine, $C_{22}H_{30}C_{12}N_{10}(H_2O)$ for water purification.

Nevertheless, the use of chlorhexidine poses special problems for filtration because the recovered fluid must be essentially pure. Chlorhexidine base is ~0.08% soluble in water at room temperature, which though it seems low, is still above the EPA's zero-solubility mandate for substances and devices used in water purification. The limit of detection for chlorhexidine in aqueous fluids is commonly in the range of 1 µg/mL (0.0001% by weight, or 0.000002 M), which is about five order of magnitude below the solubility limit. Hence, use of neat chlorhexidine for purification has not been an option for inline aqueous purification in residential and other point-of-use systems.

In any case, with or without chlorhexidine the pathogen problem has remained real and ongoing. For instance, the U.S. Centers for Disease Control (CDC) reports that the incidence of legionella has grown nine-fold since 2000, and in 2018 about 10,000 patients were diagnosed with it. The CDC suggests that this number is likely low because the disease tends to be underdiagnosed. Moreover, legionella is fatal in about 10% of the cases. However, the pathogenic contamination problem extends far beyond Lp1, as is evident from the current coronavirus pandemic, which is thought to spread in large part through air.

Thus, there is an ongoing need for systems, methods and devices that can sanitize fluids such as air and water. And there is a further need in the art for systems that can meet the minimum EPA specifications for microbicidal action without leaving significant chemical residues in fluid media.

BRIEF SUMMARY OF THE INVENTION

The invention provides systems for sanitizing fluids such as water and air. In particular, the invention provides a combination of solid chlorhexidine and a polymer matrix, for which effluents are essentially free of leached chlorhexidine. The systems enable rapid disinfecting of fluids, including in line at the point of use, and can be employed for both high volume applications and disposable single-use applications.

In particular, the present invention provides a microbicidal filtration system comprising:
a) a set of solid chlorhexidine (CX) particles having the following characteristics:
  i) a purity of at least 97.0% chlorhexidine by weight, when any presence of counterions or water molecules is factored out; and
  ii) no more than 3.0% by weight of chloroaniline impurities, when any presence of counterions or water molecules is factored out;
  iii) the CX particles are each characterized in having a releasing surface from which molecular chlorhexidine may dissolve into an aqueous medium that passes over them or dissolve into a polymer matrix that is juxtaposed at that surface.
  iv) a particle phase composition selected from the group consisting of amorphous, crystalline, and mixed amorphous and crystalline, wherein the phase composition of each particle is the same as or independent of the phase composition of a majority of other CX particles in the set;
b) a porous matrix having the following characteristics:
  i) when any presence of chlorhexidine and of chloroaniline impurities is factored out, at least 90% of the matrix by dry weight is constituted by one or more polymers that do not dissolve in water;
  ii) the porous matrix has exposed polymer surfaces that are capable of trapping chlorhexidine from an aqueous fluid in which the chlorhexidine is dissolved; and
  iii) the matrix has a permeability of at least 100 millidarcies relative to water;
c) disposal of the CX particles and porous matrix in a relative manner to form a microbicidal filter wherein:
  i) the chlorhexidine particles are permanently affixed to the porous matrix;
  ii) the affixed chlorhexidine particles comprise from 0.5% to 95% of the combined weight of the porous matrix and the chlorhexidine particles affixed thereto;
  iii) when the fluid is aqueous, release of dissolved chlorhexidine from the microbicidal filter into a flow of aqueous fluid is essentially fully counterbalanced by trapping of dissolved chlorhexidine at the exposed polymer surfaces in the porous matrix, such that at a rate of aqueous fluid flow of 0.3 to 1.3 liter/(minute*square inch) through the microbicidal filter:
    A) effluent from the filtered fluid flow is free of any detectable taste and odor of chlorhexidine;
    B) dissolved chlorhexidine, if present in the effluent, is present at less than 3.00 milligrams per liter of effluent;
    C) each of 2-, 3-, or 4-chloroaniline, if present in the effluent, is present at less than 0.100 milligrams per liter of effluent; and
    D) such full counterbalancing is sustainable for a throughput volume of at least 800 gallons of water at room temperature per cubic inch of foam in a microbicidal filter; and
d) microbicidal capacity such that, within the sustainable throughput volume at the rate of aqueous flow shown in (c)(iv)(D), the filter kills or otherwise inactivates pathogens from an influent, such that at a minimum the reduction of live cells between influent and effluent occurs to a degree selected from the group consisting of the following:
  i) a 6.6-log reduction in coliform bacteria *Escherichia coli* or *Klebsiella terrigena* for samples having $1 \times 10^7$ live cells/100 mL influent;
  ii) a 4-log reduction in a *Coronavirus* strain or process resistant viruses *poliovirus* 1 (LSc) or rotavirus (Wa or SA-11) for samples having $1 \times 10^7$ viral particles/L influent;
  iii) a 3-log reduction in cysts of *Giardia muris* or *Giardia lamblia*, for samples having a concentration in the range of $1 \times 10^6$ to $1 \times 10^7$ organisms/L influent; and
  iv) a 3.8 log reduction in a *Legionella* bacterial strain for samples having $6 \times 10^3$ live cells/L influent.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

The invention may be further understood by consideration of the drawings, each of which depicts a caricature of a non-limiting illustration of features of the invention.

DETAILED DESCRIPTION OF THE INVENTION

Definitions

Figure 1A:
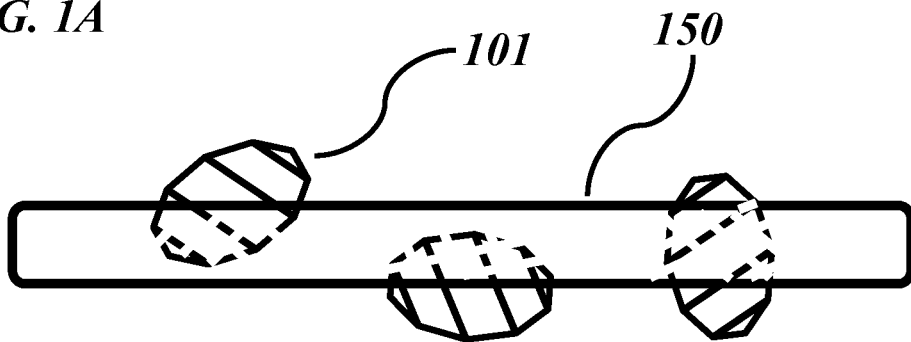
FIG. 1A depicts partial embedding of chlorhexidine particles in a polymer matrix.
Figure 1B:
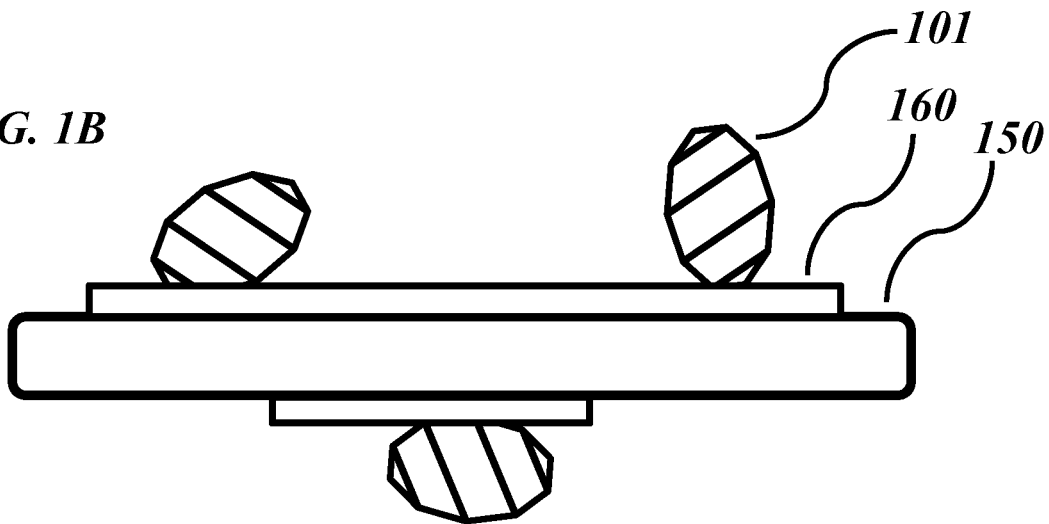
FIG. 1B depicts affixing chlorhexidine particles by adhesion polymer matrix surfaces.
Figure 1C:
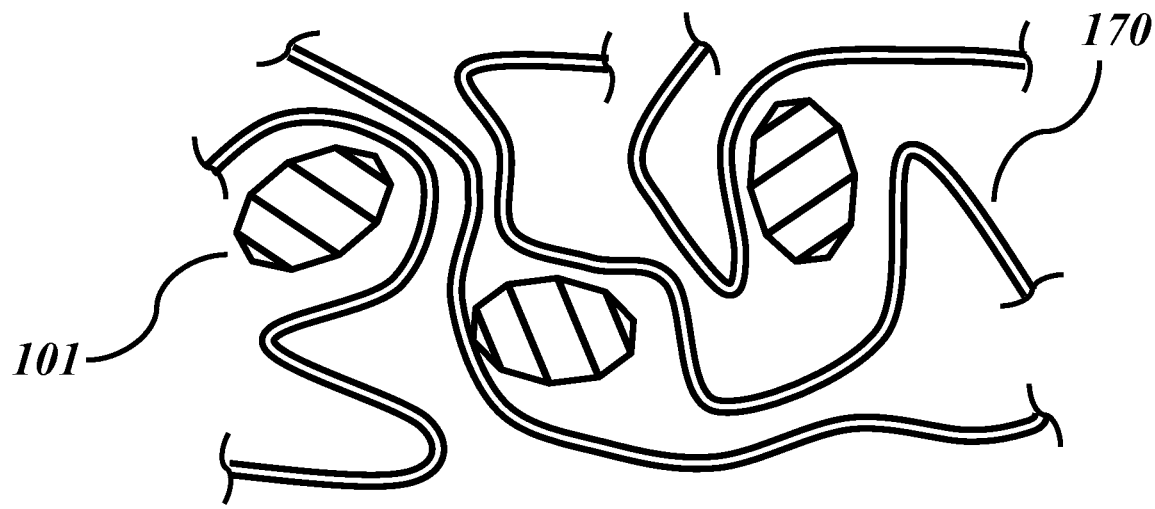
FIG. 1C depicts enmeshing of chlorhexidine particles by fibers in a polymer matrix.
Figure 1D:
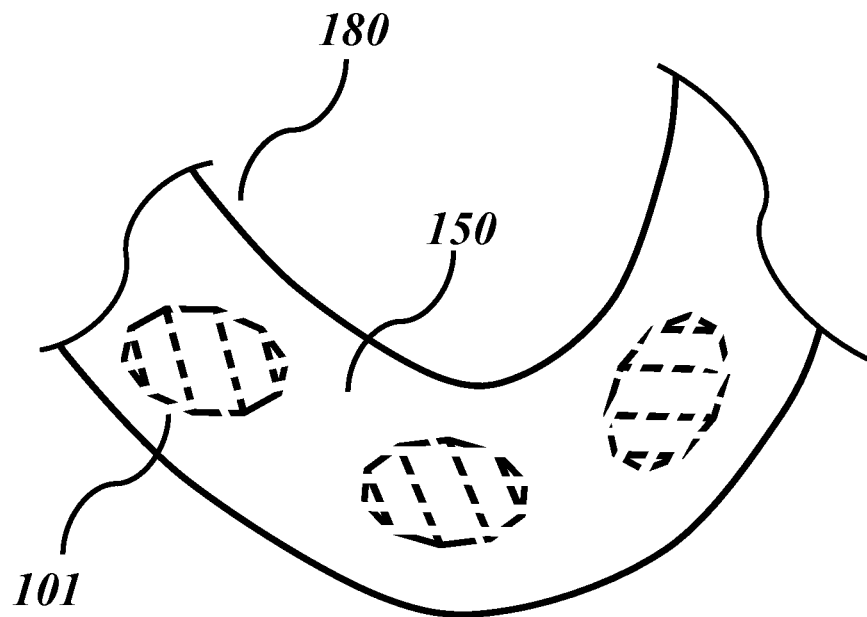
FIG. 1D depicts a polymer matrix with fully submerged chlorhexidine particles.

The following definitions clarify the scope and use of the invention including for compositions, devices and processes employing the invention.

The terms "microorganism" and "microbes" are used synonymously herein and have their usual and ordinary meaning in the biological and medical sciences, and include but are not limited to bacteria, viruses, protozoa, prions, molds, single- and multi-celled algae, single- and multi-celled yeasts, and other microscopic fungi.

The term "microbicidal" means the property of killing or destroying one or more species of microorganisms. In particular it refers to killing or destroying bacteria, fungi, viruses, protozoa, microscopic worms, or other pathogenic microbes, but the invention is not so limited.

The term "medium" means matter such as a fluid or solid, and may be a solid, a liquid solution, a suspension of solids in liquid, a gas, or some other medium. In particular media may refer to potential distributive media such as fluids being filtered to remove microbes.

The terms "filter" and "filtering" have their ordinary and common meaning in the fields of filtration for water and for air, and include but are not limited to the removal of microorganisms and other impurities from water intended for use by humans. The term "filtration medium" means a composition of matter from which a filter is constituted. In particular includes but is not limited to the process of separating particles above a threshold size from a fluid medium. The fluid may be water, air, or another fluid. The term "filtered fluid" means a fluid that has been passed through a purification material according to the invention.

The term "rigorous filtration" is used in a broad sense herein with regard to the size of excluded molecules, cells and inanimate particles. It includes microfiltration (excluding by size, with a lower cut-off range of 0.1 to 10 microns, or above $10^6$ Da); dialysis methods and ultrafiltration (molecular weight cut-off in the range of $10^3$ Da to $10^6$ Da); nanofiltration (excluding molecules with a lower size range of 1 to 10 nm); osmosis; reverse osmosis (excluding even smaller particles); and the like. In various embodiments the lower threshold for exclusion by size is selected from one of the following ranges: 10 microns, 1 micron, 0.1 micron, $10^6$ Da, $10^5$ Da, $10^4$ Da, $10^3$ Da, $10^2$ Da, 10' Da, 10 nm and 1 nm. In particularly useful embodiments the rigorous filtration is at the level of ultrafiltration, or excludes particles $\geq 0.2$ microns in diameter, but the invention is not so limited. The term "rigorous filtration medium" means a composition of matter from which a filter is constituted by which rigorous filtration is performed.

The term "microbicidal filtration system" means a system for removing, killing, and or damaging microscopic organisms in a fluid.

The term "microbicidal filter" means a unit for microbicidal filtration. It may be a modular component such as a filter pad that may be arrayed with others in series within a housing. In some embodiments the housing and pad(s) therein may together be cited as a filter.

The terms "chlorhexidine" and "CX" are synonymous and mean the compound having the chemical designation 1,6-bis(4-chloro-phenylbiguanido)hexane. The term "chlorhexidine substance" means a composition having chlorhexidine as a component and includes but is not limited to chlorhexidine, its salts, its hydrates, and combinations thereof. The terms "chlorhexidine hydrate" and "CXH" are synonymous and refer to chlorhexidine that has some number of waters of association, irrespective of whether the value of that number is an integer, fraction or other number. The term "chlorhexidine salt(s)" refers to chlorhexidine that is associated with a counterion; generally but not always, such salts are acid salts wherein the chlorhexidine is positively charged due to bonding with one or more acidic protons and the counterion is an anion. Examples of CX salts include but are not limited to the dihydrochloride, diacetate, digluconate and dicitrate salts, as well as mixed salts with CX. In some embodiments the salts have integer ratios between the respective anion and cation; in others the ratio contains a non-integer.

The term "detectable" as used with respect to chemical content refers to concentrations that are detectable by analytical instrumentation at the date of this filing. Specific values are provided in the description of the invention. The term "detectable" as used with respect to taste and odor of chlorhexidine refers to the range that is perceivable by human users with their taste buds and or olfactory senses.

The term "solid" has its usual and ordinary meaning in chemistry, and particularly refers to compositions in the solid phase but is not so limited. The term "solids" as used with respect to particles means that the particles are composed of solid substances, and is used interchangeably with the term "particles".

The term "particle" as used with reference to either an infectious or noninfectious object means a minute piece, portion, fragment, or amount. It includes but is not limited to particles having a solid composition. Examples include but are not limited to particles comprising any of: chlorhexidine, minerals, activated carbon, other filtration materials, cells, viruses, and prions.

The term "grain" is used synonymously herein with the time term particle. In particular the term "grain" includes but is not limited to grains of phosphates of calcium, carbonates of calcium, carbon, and sand.

The term "phosphates of calcium" has its usual and ordinary meaning in chemistry. As used herein the term "phosphates of calcium" include but is not limited to species having hydrate, oxo, hydroxide, and or halide components. It may be present in a biologically formed state such as bone mineral, tooth enamel, or another such state. For example, it may be present in a colloidal micelle form as in milk, and bound by casein protein with magnesium, zinc, and citrate. Phosphates of calcium may also be provided as geologically formed minerals, whether in the pure state or admixed with phases or particles of other minerals. Illustrative non-limiting examples of phosphates of calcium and their hydrates include: monocalcium phosphate, $Ca(H_2PO_4)_2$ and $Ca(H_2PO_4)_2(H_2O)$; dicalcium phosphate also called dibasic calcium phosphate, $CaHPO_4$ (mineral: monetite), $CaHPO_4(H_2O)_2$ (mineral: brushite) and $CaHPO_4(H_2O)$; tricalcium phosphate, $Ca_3(PO_4)_2$, sometimes known by other names or as the mineral whitlockite; $Ca_3(PO_4)_2$; octacalcium phosphate, $Ca_8H_2(PO_4)_6 \cdot 5H_2O$; amorphous calcium phosphate, a biological glassy precipitate of variable composition; dicalcium diphosphate, $Ca_2P_2O_7$, calcium triphosphate, $Ca_5(P_3O_{10})_2$; hydroxyapatite, $Ca_5(PO_4)_3(OH)$; apatite, $Caio(PO_4)_6(OH, F, Cl, Br)_2$; and tetracalcium phosphate, $Ca_4(PO_4)_2O$.

The term "carbonates of calcium" refers to $CaCO_3$ and has its usual and ordinary meaning in chemistry. As used herein the term "carbonates of calcium" includes but is not limited to its: various polymorphs such as calcite, aragonite, and valerite; geological mineral formd such as limestone, chalk, marble, travertine, tufa, and the like; and biological form such as egg shells, snail shells, sea shells, clam shells, oyster shells, vegetative forms such as in broccoli or kale, and the like. The term includes forms obtained from aquatic organisms such as but not limited to: plankton, coralline algae, sponges, brachiopods, echinoderms, bryozoa, and mollusks.

The term "carbon" as used in naming solids herein refers to compositions comprising primarily the element carbon, in the sense that such solids are known in materials science. The term carbon as used herein contemplates use of any allotrope of carbon, but in particular includes carbon solids that are predominantly amorphous. Non-limiting examples of such amorphous carbons are known as soot, carbon black, black carbon, activated carbon (AC), and the like. Such materials are commonly formed from incomplete combustion of petroleum products, organic biological products, gases such as ethylene or acetylene, and products made from any of those, however the invention is not limited by the origin of such carbons. These predominantly amorphous carbons exist in classes, which are partially explained here. Soot, whether synthetic or natural, is known for its low surface-area-to-volume ratio and significant content of polycyclic aromatic hydrocarbons (PAHs). Black carbon is commonly found in soot, is fine (no more than 2.5 microns in aerodynamic diameter) and is pure carbon in a variety of linked forms. Carbon black is paracrystalline (i.e., lacking long-range ordering in at least one direction), and has a high surface-area-to-volume ratio and low PAH content. Activated carbon (AC), also known as activated charcoal or active carbon, is characterized by small pores; these increase the surface area for adsorption or chemical reactions at its exposed surfaces to even exceed 3,000 square meters per gram of AC as measured by gas adsorption. AC is often identified by its origin, e.g., activated coal or activated coke.

The term "activated carbon" (AC) has its usual and ordinary meaning in materials science. The term is not limited by its outer contours, for instance it may be powdered, granulated, extruded, in bead form, or may be impregnated, polymer coated, or woven. The term is not limited by the origin of materials that are combusted to make it, whether they are petroleum, gases, or biological materials particularly useful AC products for the present invention are obtained by combustion of coconut or rice hulls, but the invention is not so limited. The invention has found that when amorphous carbons are affixed to or otherwise held within a polymer matrix, AC appears to be about twenty times more effective than black carbon at removing dissolved contaminants than black carbon is, where the contaminants are inorganic or organic in composition; this permits use of 95% less AC by weight than the mass of black carbon needed to achieve the same effect.

The term "sand" has its usual and ordinary meaning in geology and soil science, and includes without limitation small grains of quartz and other minerals.

The term "inanimate particle" means a particle that is comprised of non-living matter. Examples include but are not limited to dead cells; portions of dead cells; inorganic debris; and organic solids that are not composed of biological tissue. The term "comparable size", as used when comparing inanimate particles to microorganisms, refers to the size of the inanimate particles relative to the size of the respective microorganisms.

The term "fiber" as used with respect to materials has its usual and ordinary meaning in materials science. Fibers are to be understood as a type of particle.

The term "set" as used with respect to particles means that they are collectively used in the formation of a porous matrix.

The term "purity" means relative freedom from adulteration or contamination.

Purity may be defined, for instance, by the weight percent of the composition being referenced. Purity may be stated as a relative condition when any incidental amount of specific other composition is factored out. Thus, the purity of chlorhexidine may be stated when for instance any presence of water or counterions is ignored or factored out. This is useful for analytical methods that characterize the amount of contaminants for a given mass of chlorhexidine, where residual traces of some substance such as water or counterions may be present from prior processing of the sample but are not regarded as endangering to the health of human users.

The term "counterion" has its usual and ordinary meaning in chemistry, and means a charged species that counterbalances a species that bears a charge of opposite polarity. The counterion may be equal but opposite, as in the case of NaCl, or may be opposite but only equal by a ratio other than one-to-one, such as in the case of $CaCl_2$. Where CX reacts with an acid or complexes with a salt, it acquires a counterion. Thus the presence of counterion must be considered or factored out when determining the true concentration of CX in media.

The term "impurity" means an adulterant or contaminant, including but not limited to an undesirable substance or organism in a fluid in dissolved or undissolved form.

The term "purification material" means a composition having the purpose of removing infectious and or noninfectious particles and or dissolved impurities from an influent by means of disinfectant reaction with the composition, mechanical size exclusion, physical adsorption to a surface, chemical absorption into the composition, or other means.

The term "disinfectant" means a microbe-destroying substance. Typically, the microbes are bacteria and the disinfectant is a liquid, but the invention is not so limited.

The term "sanitize" means to make clean and hygienic; to disinfect.

The term "chloroaniline" refers to monochloro-anilines, has its usual and ordinary meaning in organic chemistry, and refers to any of the 2-, 3-, or 4- isomer of aniline, i.e., ortho-, meta-, or para-$C_6H_4(-Cl)(-NH_2)$.

The term "water" means the chemical entity with molecular formula $H_2O$, irrespective of whether it is in the solid, liquid, or gas phase, and irrespective of whether it exists as humidity in a gas, or is chemically associated form such as a hydrate, or is physically constrained such as a clathrate in a lattice.

The term "counterions" means a negatively charged ion, irrespective of any associated cation.

The term "factored out" as used with respect to any component of a composition means that calculations as to the remainder of the composition are carried out as if that component is absent.

The term "percent by weight" refers to the percentage composition of a material as a function of weight. The term is used as opposed to percentage by volume, surface area, particle count, or other metrics. The term "by dry weight" means, by reference to the material in the absence of any water.

The term "releasing surface" as used with respect to a CX particle means a surface from which molecular CX may be dissolved into an aqueous medium that passes over that surface or dissolved into a polymer matrix that is juxtaposed at that surface. The term "dissolved" in this context means that CX molecules leave the CX particle and are held within the aqueous medium and or polymer matrix in a way that permits diffusion of those molecules. The terms "dissolved" and "dissolution" with respect to molecular CX are not limited to uncharged CX. To be clear, this invention provides solid CX in its base form, i.e., as an uncharged species and not a salt. However, even pure water commonly dissociates into protons, $H^+$, and hydroxide anions, $HO^-$, as is well known in pH studies. In the presence of such ions a significant fraction of the amine and imine nitrogens of chlorhexidine are expected to bond with the protons at least transiently to form a chlorhexidinium hydroxide salt, and such a salt will be more soluble in that aqueous medium than uncharged CX would be. Moreover, some of the CX nitrogens and the hydrogen atoms to which they are covalently bonded would be expected to participate in hydrogen bonding with the hydrogen and oxygen respectively, of neutral water. Thus in the context of dissolved species, the terms "molecular chlorhexidine" and "dissolved chlorhexidine" include both salts and hydrates that form by reaction with the fluid medium, or for instance otherwise react with water that is in the immediate environment of CX solids. Comparable phenomena may occur when the CX reacts for instance with moieties of polymers such as for instance, pendant carboxylic acids or pendant hydroxyls, or when it reacts with water that swells a polymer matrix; such interaction is contemplated within the scope of the invention.

The term "passing over" a releasing surface, as used with respect to a fluid, means that the fluid flows directly on, over, along, or otherwise directly exposed to that surface as the fluid passes by.

The terms "dissolve" and "dissolution" have their usual and ordinary meaning in the field of chemistry. In particular, the term "dissolved" refers to a substance to the extent that the respective molecules and/or ions are physically dispersed in a surrounding medium as a solute. Examples of organic solutes include but are not limited to chlorhexidine substances. Examples of inorganic impurities dissolved in influent include but are not limited to: trivalent arsenic, pentavalent arsenic, hydrogen sulfide, iron, copper, zinc, lead, aluminum, chromium, uranium or a combination thereof.

The term "essentially fully counterbalanced" as used with respect to chlorhexidine dissolved into a flow of aqueous fluid from a releasing surface and then trapped at an expose polymer surface means that the rate of trapping—such as by adsorption, absorption, chelation, and or the like—is sufficiently great and sustainable to remove chlorhexidine such that no more than a trace amount remains in the water. By "trace amount" of chlorhexidine is meant, an amount so low that it leaves no taste or odor in the effluent. In particular a trace amount means an amount selected from no more than: 0.0003% by weight; 0.0001% by weight; and 0.000068% by weight. In a further embodiment, any residual chlorhexidine in the aqueous effluent is present at under 3.00 milligrams per liter of effluent. In certain embodiments the extent of removal may be further quantified by specification, such as but not limited to characteristics at a rate of aqueous fluid flow of 0.3 to 1.3 liters per (number of minutes of flow x square inches of filter area that is oriented transverse to the flow through the filter). In certain embodiments, the same counterbalancing mechanism is sufficient to remove any 2-, 3-, or 4-chloroaniline that is released, such that less than 0.100 milligrams of the respective chloroaniline remains per liter of effluent.

The term "trapping" as used with respect to trapping chlorhexidine or chloroaniline in a fluid, such that they are trapped by an exposed polymer surface, means that the surface removes the chlorhexidine or chloroaniline from the fluid by some mechanism. Such mechanisms may be absorption, adsorption, physical trapping in a nanoscopic pore, chemical reaction, or any other mechanism by which molecules are removed from fluids by solid matrices through which the fluids pass.

The term "sustainable" as used with respect to essentially full counterbalancing, means that it is sustainable relative to a particular lifecycle specification. In particular the "throughput volume" for such a specification, i.e., the volume of fluid through a filter system of the present invention, may be designated by the number of gallons of water that may be passed through it at a designated temperature per cubic inch of foam in a microbicidal filter before the filter should be replaced. As an example, 800 gallons of water at room temperature per cubic of foam may be a specification. Alternatively or in addition, filters of the invention may be provided designed for other capacities, or for treatment at higher or lower temperatures.

The terms "trivalent arsenic," "pentavalent arsenic," "hydrogen sulfide," "iron," "copper," "zinc," "lead," "aluminum," "chromium," and "uranium" have their usual and ordinary meaning in chemistry. Where no charge state, oxidation state, or valency count is indicated, these terms include together or separately any relevant such state or count for the respective referenced sub stance.

The term "purifying substance" as used with respect to removal of inorganic impurities from influent means a substance for their adsorption, absorption, chelation, or other means for their removal. Non-limiting examples of such purifying substances include calcium phosphates, bone char, sand, activated carbon, and the like. The capacity and efficiency of removal may be specified. In a non-limiting illustrative example of such as specification, a purifying substance is provided in a sufficient quantity to remove from influent at least 50 percent by weight of at least one named inorganic impurity, for at least 800 gallons of room temperature water per cubic inch of foam in a microbicidal filter. In various embodiments the lower threshold for removal of the named inorganic substance is at least one of the following: 50%; 55%; 60%; 65%; 70%; 75%; 80%; 85%; 90%; 95%; 96%; 97%; 98%; 99%; 99.5%; 99.9%; 99.99%; or 99.999%. In various embodiments the lower capacity in gallons of water for removal is at least one of the following: 100; 200; 300; 400; 500; 600; 700; 800; 900; 1000; 1100; 1200; 1300; 1400; 1500; 1600; 1700; 1800; 1900; 2000; 2500; 3000; 3500; 4000; 4500; or 5000 gallons.

The term "phase composition" as used with respect to a particle refers to its molecular organization. In particular, a solid particle may be amorphous, crystalline, or have a mixture of amorphous and crystalline respective phases. In various embodiments the phase composition of a given particle may be the same as, different from, or independent of the phase composition of a majority of other CX particles surrounding it.

The term "amorphous" has its usual and ordinary meaning in chemistry and materials science, and in particular denotes the substantial absence of crystallinity in a referenced phase or domain of a material.

The terms "crystalline" and "crystal" have their usual and ordinary meaning in polymer science and organic chemistry, and in particular denote an orderly array of polymers in a referenced phase or domain of a material. Note that although polymers can embed materials, the crystalline portions of polymers tend to be discrete, relatively pure crystallites as that term is commonly understood to mean phase domains in polymer science and engineering.

The term "porosity," when used in reference to pore sizes, refers to the average diameter of the pores. Purification materials having pore sizes in the range of 200-800 microns in diameter are particularly useful according to the invention, but the invention is not so limited.

The term "in porous form," when used in reference to compositions according to the invention, means that the material has sufficient porosity to be permeable.

The term "permeability" means the ability of a material to allow passage of a fluid through it. In particular, it means that the material has pores of a suitable size and population density to enable the material's use as a rigorous filtration medium. This may vary depending on the viscosity and or other properties of the fluid. A common scientific unit for permeability is the darcy; a material with permeability of 1 darcy allows a flow of 1 $cm^3/s$ when the fluid has 1 centipoise viscosity (i.e., approximately that of water at 20° C.) under a pressure gradient of 1 atmosphere/cm acting upon a 1 $cm^2$ area. 1 darcy is equivalent to 0.831 m/day (i.e., 0.00000139279 cm/s), which are alternative units for representing permeability or hydraulic conductivity. Compositions having a permeability of at least 100 millidarcys allow the facile passage of a fluid. In particular, with respect to embodiments of mixed particulate compositions according to the invention for the filtration of water, such embodiments have a permeability of at least 100 millidarcys, at least 1,000 millidarcys, at least 10,000 millidarcys, at least 100,000 millidarcys, or at least 1,000,000 millidarcys.

The term "matrix" means a medium employed in filtration. A matrix may be constituted by a single material or plurality of materials. In particular embodiments a matrix is comprised of a material selected from the group consisting of synthetic polymers, natural polymers, ceramics, glasses, metals, metal oxides, stone-based materials such as for example sand or granite or calcium oxide, black carbon, bone-based materials, and calcium phosphates, but the invention is not so limited.

The term "porous matrix" means a matrix that is in porous form. In various embodiments the porous matrix comprises one or more of the following: an open foam; a reticulated foam; a fiber mat; a knitted fabric; a woven fabric; a nonwoven fabric; a material formed by sintering; a material formed by particles attached to one another by a binder; and a monolithic solid in which are defined channels running through it. In particular embodiments a porous matrix may be comprised of an upstream zone within which chlorhexidine particles are permanently affixed and a downstream zone that is essentially free of chlorhexidine particles.

The terms "open foam" and "open cell foam" are synonymous and mean a foam comprised of open cells through which a fluid may pass. In some embodiments it is bread-like, such that microbes present in a fluid filtered by the foam pass through in a tortuous path.

The term "reticulated foam" means an open foam that is net-like on close inspection, wherein few if any bubbles or cell windows remain intact.

As used with respect to fabrics the terms "fiber", "knitted", "woven", and "nonwoven" have their usual and ordinary meaning in fabric production.

The term "sintering" means producing particle coalescence, such as by full or partial melting of a powder. Use of a binder and use of monolithic solids with channels is clarified elsewhere herein.

The term "upstream" as used to characterize a zone or other feature means that the zone or feature is encountered earlier in a flow sequence than is another referenced feature.

The term "downstream" as used to characterize a zone or other feature means that the zone or feature is encountered later in a flow sequence than is another referenced feature.

The terms "porous block" and "porous sheet" as used with respect to purification materials refer to compositions in which channels of some size exist within solid blocks or sheets. Such blocks or sheets may be rigid, or alternatively may be flexible, or any combination or gradient thereof.

The terms "polymer" and "polymeric" have their usual and ordinary meanings in polymer science and engineering. This includes but is not limited to synthetic polymers, natural polymers, thermosets, thermoplastics, rubbers, elastomers, random copolymers, block copolymers, dendritic polymers, comb polymers, branched polymers, cross-linked polymers, organometallic polymers, ionomers, electrically conducting polymers, ionically conducting polymers, polyelectrolytes, condensation polymers, polymers formed by chain reaction, polymer blends, interpenetrating polymers, and the like.

The terms "water-insoluble" and "do not dissolve in water" as used with respect to polymers are synonymous and means that thusly designated polymers do not dissolve in pure water at room temperature at a ratio of 1% polymer to 99% water by weight. Merely swelling in water or forming a gel in the presence of water is not deemed to be dissolving in water for the purposes of this invention. The critical point for instability of aqueous polymer solutions under Flory-Huggins solution theory is deemed to be the threshold for water solubility here, such as is well-known in the arts of polymer science and engineering. The water-insoluble polymers may optionally be selected from among polyurethanes, polyolefins, polyesters, polycarbonates, synthetic or natural polyamides, polyimides, polyacrylates, polymethacrylates, vinyl polymers, rubbers, polyacrylonitrile, polysiloxanes, polysaccharides, as those terms are defined in the arts of polymer science and engineering. The water-insoluble polymers may be combinations or blends of any of those. However, the invention is not limited by the chemical identity of the water-insoluble polymer(s). The water-insoluble polymers may be in any macroscopic foam, and particularly in the form of a foam.

The terms "melting transition temperature" and "glass transition temperature" as used with respect to a polymer has their usual and ordinary meanings in polymer science and engineering, and correspond to the properties conventionally designated by $T_m$ and $T_g$.

The term "exposed" as used with respect to a polymer surface in a matrix means that the surface is or would be in direct contact with a fluid that passes through the matrix. The term "exposed" as used with respect to fluid exposed to a CX solid means that that solid is or would be in direct contact with a fluid passing over it. Such exposures by a fluid may be simultaneous, such as where CX solids are disposed on the matrix. Alternatively or in addition, exposures by a fluid may be sequential, such as where CX solids are disposed in a module through which fluid flows prior to passing through a module containing the matrix.

The term "aqueous" as used with respect to a medium or fluid means that the substance so designated is liquid and contains water, without respect to pH. In various embodiments the term "aqueous" refers to liquids containing at least 1%, 10%, 25%, 50%, 75%, 90%, or 99% water. In some preferred embodiments the liquid comprises at least 99% water.

The term "fluid" means a liquid, a gas, or a combination thereof. The fluid optionally has solutes dissolved therein or has a suspension of small solids. In some embodiments the fluid comprises one or more liquids from the following group: water, ethanol, isopropanol, an aqueous solution, a mixture primarily comprising water and ethanol, blood, a bodily fluid other than blood, a microbial fermentation broth, and mixtures thereof. In additional embodiments the fluid comprises one or more gases from the following group: air, oxygen gas, nitrogen gas, carbon dioxide, argon gas, nitrous oxide, an anesthetic gas other than nitrous oxide, and mixtures thereof. Names for each of these illustrative fluids are used as understood in the arts of chemistry and medicine. Where the fluid is an aqueous medium, in certain embodiments it is one or a combination of: potable water, a beverage, a recycle stream in a chemical process, a recycle stream in a cell culturing process, an aqueous solution that has been used in a surgical procedure, and mixtures thereof. It is to be understood that the invention contemplates filtering fluids for consumption, prophylactic or therapeutic use, diagnostic use, sanitation, resource recovery, culturing of cells or biological specimens, and other uses.

The term "capable of adsorbing chlorhexidine from an aqueous fluid in which the chlorhexidine is dissolved" as used with respect to a polymer matrix means that the matrix is capable of forming surface attractions to aqueously dissolved chlorhexidine and thereby removing it from that fluid. "Adsorption" as used herein refers to surface adsorption, as opposed to absorption of a substance into the interior of a matrix solid by its diffusion or transport therein.

The term "disposal" as used with respect to CX particles at a porous matrix refers to the way in which the particles are placed and or distributed within that matrix. Disposal of the particles "in a relative manner" with respect to the matrix refers to their relative physical orientations. For instance, particles may be disposed to lie juxtaposed against otherwise exposed surfaces of the matrix such as by an adhesive substance or adhesive bond, or may be partially embedded within the matrix, or may be disposed on one side of a filter pad constituting the matrix, or may be fully submerged within the matrix material.

The term "diameter" as used herein is to be interpreted within its context. The term "diameter" as used with respect to particular particles refers to the diameter that corresponds to spheroids having the same volume as the respective particles. This approximation is well-known and widely used in the science and engineering of sieves due to the diversity of sieved particle shapes and wide range of their dimensional aspect ratios even within the same sample. The invention is not limited to the use of sieves to determine particle sizes and particle size distribution via mesh size. Non-limiting examples of other methodologies for these determination include ultrasound methods, electric field methods, gravity methods, centrifugation methods, dynamic imaging analysis, inline image analysis, and the like. Using the sphere approximation, $D=2*[(3V)/(4 \pi)]^{1/3}$ where V is the particle's own volume and D is the diameter of an imaginary sphere having the same respective volume; as seen from the superscript the fraction is taken to the one-third power. Note that spheres are modeled as substitute because their shape and diameter are universal for any given volume. The term "average diameter" as used for a plurality of particles means the value for their respective thusly modeled spheres.

The term "diameter" as used with respect to a pore's size refers to the pore's inner diameter and is to be understood in terms of the largest diameter of particle that could pass through it. The term "average diameter" as used for a plurality of pores means the value for their respective inner diameters. The average diameter can be obtained in porosimetry, for instance by modeling a porous matrix using the reduced form of Washburn's equation as if the matrix had cylindrical pores: $D_P=1470$ kPa/$(P_L*\mu m)$ where $D_P$ is the pore diameter and $P_L$ is the pressure of liquid passing through it.

The term "fluid flow" means the motion of fluid, which may be passive as under the force of gravity or capillary action, or may be forced by a pump or vacuum or other mode of flow. The term "fluid flow into and out of," as used with respect to materials, refers to permeation of the fluid through such materials. The terms "inline" and "in line with" as used with respect to such flow through a permeable component means that the flow passes serially through stages, and that the referenced component receives it at one stage and that the flow subsequently exits from the component.

The term "influent" refers to a fluid that is directed through a filtering medium.

The term "influent flow" with respect to a purification material means the passage of influent into and through that material.

The term "effluent" refers to a fluid that has been passed through a filtering medium. The term "effluent flow" with respect to a purification material means the exit of filtered fluid from that material.

The term "upstream from" as used with respect to disposal of chlorhexidine particles relative to a porous matrix means that influent passing through the matrix comes into contact with the particles before it comes into contact with a portion of the matrix that traps chlorhexidine that has dissolved from those particles into the influent.

The term "permanently affixed" as used with respect to chlorhexidine particles affixed to a porous matrix means that the particles are firmly held to or by the matrix such as by: covalent, ionic, or hydrogen bonds between CX surface molecules and the matrix; the presence of an adhesive between the solid and a matrix surface; adhesion to a matrix surface by a melt step; partial or full embedding within the matrix; and physical retention by fibers of the matrix.

The term "air" has its usual and ordinary meaning in the atmospheric sciences. In particular it includes but is not limited to air such as is breathed by humans in ordinary living. The term air further comprises gas mixtures such as those used in tanks for underwater breathing apparati, high-altitude breathing apparati, medical breathing apparati, and the like.

The term "relative humidity" as used with respect to air has its usual meaning in the atmospheric sciences. In various embodiments it includes relative humidity of at least: 20%, 25%; 30%; 35%; 40%; 45%; 50%; 55%; 60%; 65%; 70%; 75%; 80%; 85%; 90%; 95%; or 100%.

The term "adhesive" as used with respective to substances has its usual and ordinary meaning in the chemical arts. The term "adhesive" as used with respective to an attribute means that the thing referred to forms surface bonds to hold a second item in close proximity. Non-limiting illustrative examples of adhesion as an attribute include adhesion obtained by sonication or melt processing to adhere a polymeric solid to another polymeric solid, or to a metal or alloy, or to a surface of another solid that does not melt at the processing temperature. The term "adhesive" includes uses that affix CX solids to matrix surfaces.

The terms "covalent", "ionic", and "hydrogen bond" have their usual and ordinary meaning in chemistry. In particular embodiments of the invention, one or more of such types of bonds are formed between CX solids and matrix surfaces.

The terms "embed" and "embedding" as used with respect to retention of a CX solid within a matrix material mean that the CX solid is submerged in the matrix material thereby affixing the solid in place by adhesion to and or physical trapping of that solid. The embedding may be partial, i.e., the CX solid may be less than entirely covered over by the matrix material. Or the embedding may be full, meaning that the matrix material entirely surrounds the CX solid.

The term "physical retention by fibers" as used with respect to retention of a CX solid within a matrix means that the matrix is fibrous, and that the CX solid is at least partially submerged among the fibers such that it is trapped by them there.

The term "in close proximity" as used with respect to binding of CX solids together, and with respect to fluid retention near such CX particles, means that separation of the bound solid or retained fluid relative to a reference CX particle is no more than 1 millimeter.

The term "binder" as used herein means a substance that acts as a glue or cement to hold solids together in close proximity, and in particular to hold solid particles together. The term binder is used herein irrespective of its chemical composition: it may be organic, inorganic, metallic or any permutation or combination thereof. The term binder includes but is not limited to thermoplastic, thermoset and elastomeric polymers. In some embodiments the binder absorbs moisture, whether at ambient temperature or at elevated temperatures. In certain embodiments the binder is superabsorbent.

The term "superabsorbent" as used with respect to binders and polymers has its usual and ordinary meaning in the art of absorbent polymers. In particular superabsorbent polymers may be used in the invention to place and retain water in close proximity to CX particles.

The term "hygroscopic" as used with respect to a salt means that under ambient conditions the salt is capable of attracting and holding water molecules from the surrounding environment. The environment may be air or a liquid medium. The salt may be monovalent or multivalent, and may be monomeric, oligomeric, or polymeric. The water attraction and retention mechanism may include adsorption, absorption, hydrate formation, and or other phenomena. In certain embodiments the salt is capable of attracting and holding a mass of water molecules relative to its dry weight of at least: 1%; 2%; 3%; 4%; 5%; 6%; 7%; 8%; 9%; 10%; 15%; 20%; 25%; 30%; 35%; 40%; 45%; 50%; 60%; 70%; 80%; 90%; 100%; 150%; 200%; 300%; 400%; 500%; 600%; 700%; 800%; 900%; or 1,000%.

The term "insoluble" as used with respect to a salt in water means that at room temperature at a ratio of 1% salt to 99% water by weight, no more than 1 part in 100 of the salt (1% of the salt portion) by weight is dissolved in the water.

The term "intermingled" as used with respect to a plurality of purification materials means that they have been combined in an intimate mixture. The term is not limited to homogeneous mixtures; the intimate mixtures may optionally have heterogeneous character.

The terms "mixture" and "admixture" are used interchangeably herein, and refer to physical combinations to the extent that the components retain their original chemical identities. Non-limiting illustrative mixtures include blends, solutions, suspensions and colloids.

The term "composite form" refers to a mixture and in particular a mixture of solids.

The term "sufficient to accomplish", when used in reference to an amount of CX reducing the number of microorganisms or infectious particles to any particular extent, means that upon exposure of such quantities of influent to that amount of CX, the respective microorganisms or infectious particles are removed to at least that extent within an operational period for exposing an aliquot of the fluid.

The term "sufficient to ensure", when used in reference to an amount of polymer in a matrix in a microbicidal system essentially completely removing dissolved CX from that system, means that the amount of polymer included is sufficient to essentially completely adsorb or otherwise trap any dissolved CX or eroded granular CX from the system's provided solid CX during filtration of a corresponding fluid through the purification material, such that essentially no CX exits in the effluent.

The term "essentially free of", when used with respect to CX in the effluent of a microbicidal system, means that the effluent has no taste or odor of chlorhexidine, and that there is no more than a trace amount of CX in that effluent, and in particular a trace amount means an amount selected from the group consisting of no more than: 0.0003% by weight; 0.0001% by weight, and 0.000068% by weight. The term "essentially free of", when used with respect to CX particles in a zone of a porous matrix, means that there is no more than a trace amount of CX in that zone of the matrix, and in particular a trace amount means an amount selected from the group consisting of no more than: 0.0003% by dry weight; 0.0001% by dry weight, and 0.000068% by dry weight. The term "essentially free of", when used with respect to chloroanilines, means that there is no more than a trace amount of them present in composition in view, and in particular means less than 60 micrograms per liter for each of 2- and 3-chloroaniline, and less than 57 micrograms per liter for 4-chloroaniline. That corresponds respectively to <60 ppb or <0.000006%, and <57 ppb or <0.0000057%.

The term "microbicidal capacity" refers to the extent to which pathogens within an influent are killed or otherwise inactivated when passing though a filter. This may be expressed by the number of orders of magnitude by which live cells are decreased ("n-log reduction") during the process, for a filter's effluent relative to its influent.

The term "n-log reduction", where n is a number and the term is used in reference to numbers of organisms or infectious particles per volume unit of influent, means that after purification the fluid has $10^{-n}$ times the number of live organisms or (e.g., in the case of viruses or prions) infectious particles, that were present in the influent prior to purification. The term multi-log reduction means a reduction by more than one order of magnitude, i.e., reduction in quantity by more than one power of ten. The term "reduced" as used with reference to an impurity concentration in a filtered fluid, means by comparison to that impurity's concentration in the influent prior to purification. The term "organism", as used with respect to log reductions, means an undesirable biological organism in the influent. The units L and mL (or ml) are liter and milliliter, respectively.

The scientific names for microorganisms and their life-cycle states have their usual and ordinary meaning in the fields of medicine, microbiology, water purification; and health and sanitation. These include but are not limited to: coliform bacteria; *Escherichia coli*; *Klebsiella terrigena*; process resistant viruses; enveloped viruses; poliovirus; rotavirus; cysts; *Giardia muris*; *Giardia lamblia, Legionella pneumophila* strain 1; and coronaviruses.

The term "regeneration" as used with respect to purification materials refers to treatment by which their purification capacity is recaptured in whole or in part. Non-limiting illustrative examples of regeneration means include sterilization protocols comprising at least one of elevated temperature, elevated pressure, radiation, a chemical oxidant, a chemical reductant, electrochemical treatment, and combinations thereof.

The term "sterilization conditions" refers to sanitation protocol conditions by which microorganisms in influent are killed. The term "stable under sterilization conditions" as used with respect to a binder for filtration media means that the binder remains substantially intact and functional as a binder when exposed to such conditions.

Figure 1E:
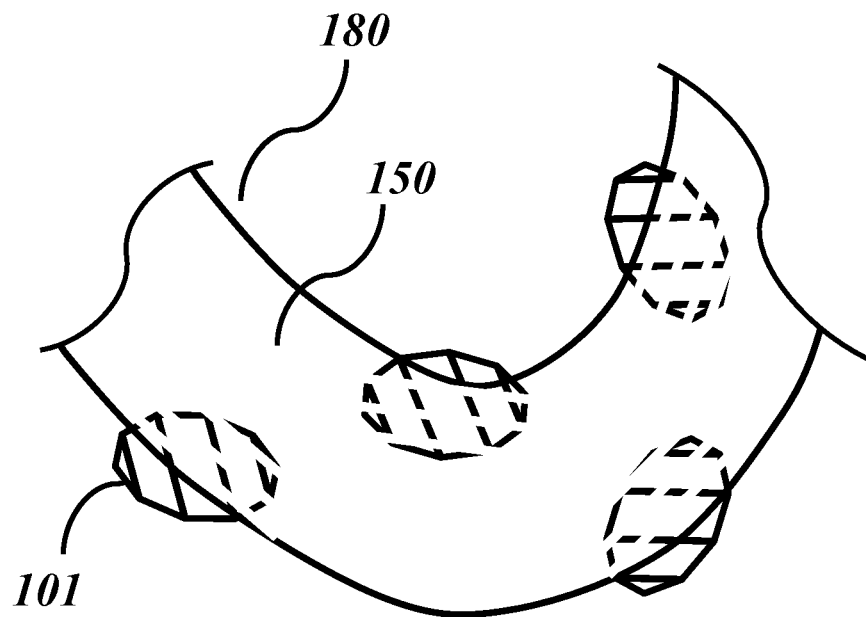
FIG. 1E depicts a polymer matrix with partially submerged chlorhexidine particles.

With respect to a filtration system, the following terms apply. A "supply module" means an apparatus or portion thereof for providing a flow of fluid ("influent fluid") for filtration. A "treatment module" means an apparatus or portion thereof for receiving that fluid, treating it by exposure to CX solids, and passing the fluid through the porous matrix simultaneously (e.g., the CX solids are disposed on the matrix) and or in order (i.e., the fluid is exposed first to CX solids and then to the porous matrix). When the exposure is in order, at least a portion of the CX solids are understood to be separate from, outside of, and in advance of the porous matrix relative to the flow of fluid through the solids and matrix. An "exit module" means an apparatus or portion thereof for receiving the fluid after treatment ("effluent," synonymous to "purified fluid") and then directing ("channeling") it or alternatively delivering it such as by carrying or other delivery means, for storage, for immediate use by an end user, or for further processing such as further purification or other processing. Consequently, "delivery" of the purified fluid to its point of use means directing its flow to there and or transporting it to there. "Point of use" means the place at which the fluid is used, such as for instance a water tap, shower head, air tank, breathing mask, or other point of use.

The term "housing" has its usual and ordinary meaning for devices, and means a surrounding structure for components. The terms "inlet" and "outlet" refer to portals for the ingress and egress of fluid through the housing, respectively. The term "contacting chamber", when referenced as being disposed between an inlet and an outlet, means that the flow passes through such chamber while within the housing.

The term "batch process" as used with respect to fluid purification or other treatment means that one or more portions of the fluid are treated as a discrete batch, as opposed to by treatment of a continuous flow of the fluid.

The term "continuous" as used with respect to fluid purification or other treatment means that a stream of the fluid is treated in a continuous fashion.

The term "configuration" as used with respect to configuring a filtration system for a particular type of method, device, or operation means that the system is physically arranged and or programmed for such functioning; nonlimiting examples include for batch and continuous processes.

The term "unit" as used with respect to comprising a filtration system of the present invention means a facility, device, module, or filter that houses the system. Nonlimiting illustrative units include the following as these terms are commonly and ordinarily understood in the art of fluid filtration: a water treatment facility for multiple end users; a point-of-use filter on plumbing for potable water; a drinking straw; a feature for purification of a fluid during its storage; a mask for breathing purified air; a filter for a ventilation system; a showerhead; a vaporizer for medical use; a sports mister for cooling; a filter for a fluid supplied to a fermentation broth; a filter for a bodily fluid; and a filter for a medication-containing fluid. In particular, "drinking straw" means a tube by means of which water or a beverage or air may be sucked from a reservoir such as a cup or another container. "Fermentation broth" means a liquid within which microorganisms are cultured; non-limiting examples include beer, wine, and broths for production of medicines from microbes. In general, the invention can be used to disinfect fluids for use in any sprayer for any purpose.

The term "residence" refers to a structure within which one or more persons live. The term "office" refers to one or more rooms or a building, that are used as a place for commercial, professional, or bureaucratic work. The term "production facility" refers to a structure within which one or more persons or machines generate products. The terms "hospital", "cruise ship" and "water treatment plant" have their usual and ordinary respective meanings in common use.

The invention may be further understood by consideration of the figures, which show features of the invention in caricature. Note that the shapes and the relative sizes of the depicted CX particles, mineral particles, activated carbon particles, and binder portions are not intended to represent the actual shapes or actual relative sizes of those particles or binder portion.

FIGS. 1A, 1B, 1C, 1D and 1E depict caricatures of chlorhexidine particles 101 that are affixed in in non-limiting illustrative ways to a polymeric substrate that is part of a porous matrix. In FIG. 1A the particles 101 are partially embedded in a polymeric material 150. In FIG. 1B the particles 101 are held to the surface of a polymeric material 150 by an adhesive layer 160. In FIG. 1C the particles 101 are held within a mat of fibers 170, being captured physically but not bonded chemically to the fibers. In FIG. 1D the particles 101 are fully submerged and entirely embedded within a polymeric material 150; the figure shows a segment of a porous matrix 180. In FIG. 1E the particles 101 are partially submerged within a polymeric material 150; the figure shows a segment of a porous matrix 180.

Figure 2A:
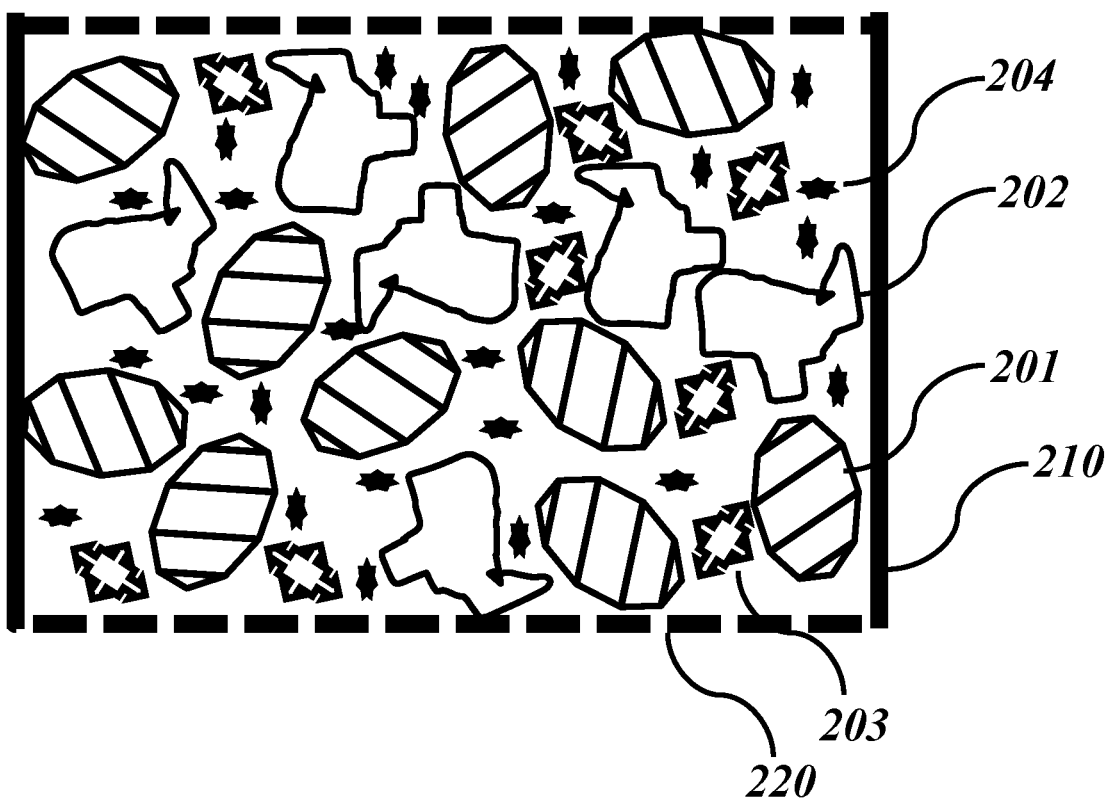
FIG. 2A depicts a mixture of particles of chlorhexidine and other solid substances for purifying fluids in a flow-through housing in a manner according to the invention.

FIG. 2A depicts a caricature of a non-limiting illustrative embodiment of a housing comprising a mixture and system according to the invention, in which a housing 210 has porous end wall(s) 220, and contains a mixture such as chlorhexidine substance CX 201, a calcium phosphate compound CPC 202, sand 203, and activated carbon 204. For ease in viewing these features, no polymer matrix is depicted though it is present.

Figure 2B:
FIG. 2B depicts a mixture of particles of chlorhexidine and other solid substances, additionally provided with a binder, the mixture being intended for purifying fluids in a manner according to the invention.

FIG. 2B depicts a caricature of a non-limiting illustrative embodiment of a mixture according to the invention in which binder is incorporated, which is useful in the preparation of porous monolithic blocks and porous flexible sheets for use as filters. Specifically, FIG. 2B depicts CX 201, a calcium phosphate compound CPC 202, sand 203, activated carbon 204, and binder 205. For ease in viewing these features, no other polymer or matrix is depicted though it may be present.

Figure 3:
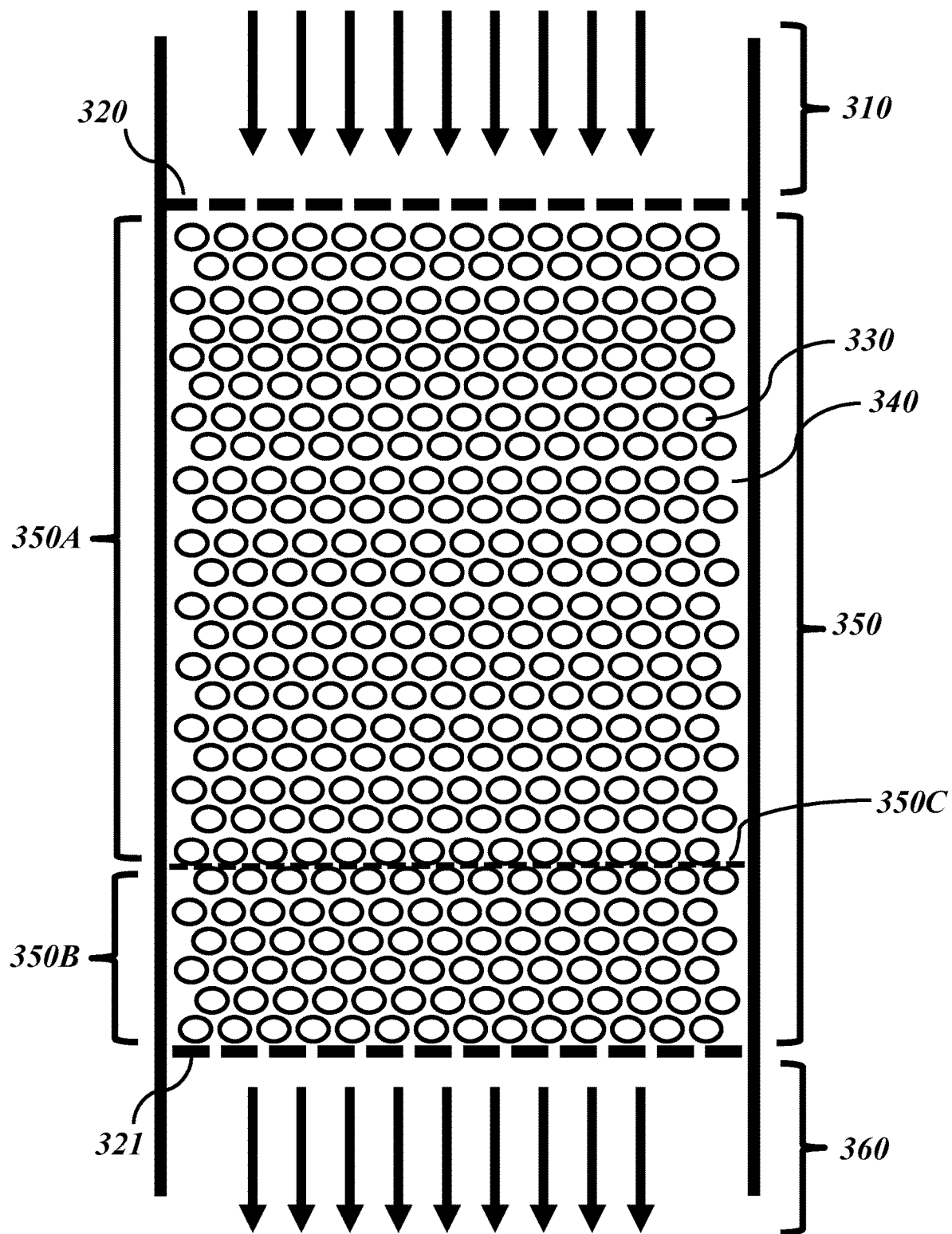
FIG. 3 depicts a system for fluid purification according to the invention.

FIG. 3 depicts a caricature of a non-limiting illustrative embodiment of a purification system according to the invention, particularly including in succession: a fluid influx zone 310; optional porous plates 320 and 321 as separators between the zones; a porous polymeric matrix 340 containing pores 330, the matrix being held within a filtration zone 350; and a fluid efflux zone 360 conveying purified fluid. Where porous plates are not used, the matrix may be held in place by a tight fit or by, for instance, being blow-molded in place with internal tabs on the housing to immobilize the resulting foam. For ease in viewing these features, no CX particles or other substances are depicted though they may be present. The features shown may be formatted in a filter cartridge, filtration module, drinking straw, air purifier, or other fluid-flowing purification device. For added security in removing CX from flow water, the porous matrix 350 may optionally be provided with two zones and optionally as either a monolithic single matrix or two juxtaposed separable matrices, wherein upstream zone 350A is embedded with CX and downstream zone 350B is prepared in a manner that is free of CX. In FIG. 3 the boundary 350C between the two zones may be either a surface between two separable blocks of foam, or may be a transition occurring within a monolithic block of foam.

Figure 4:
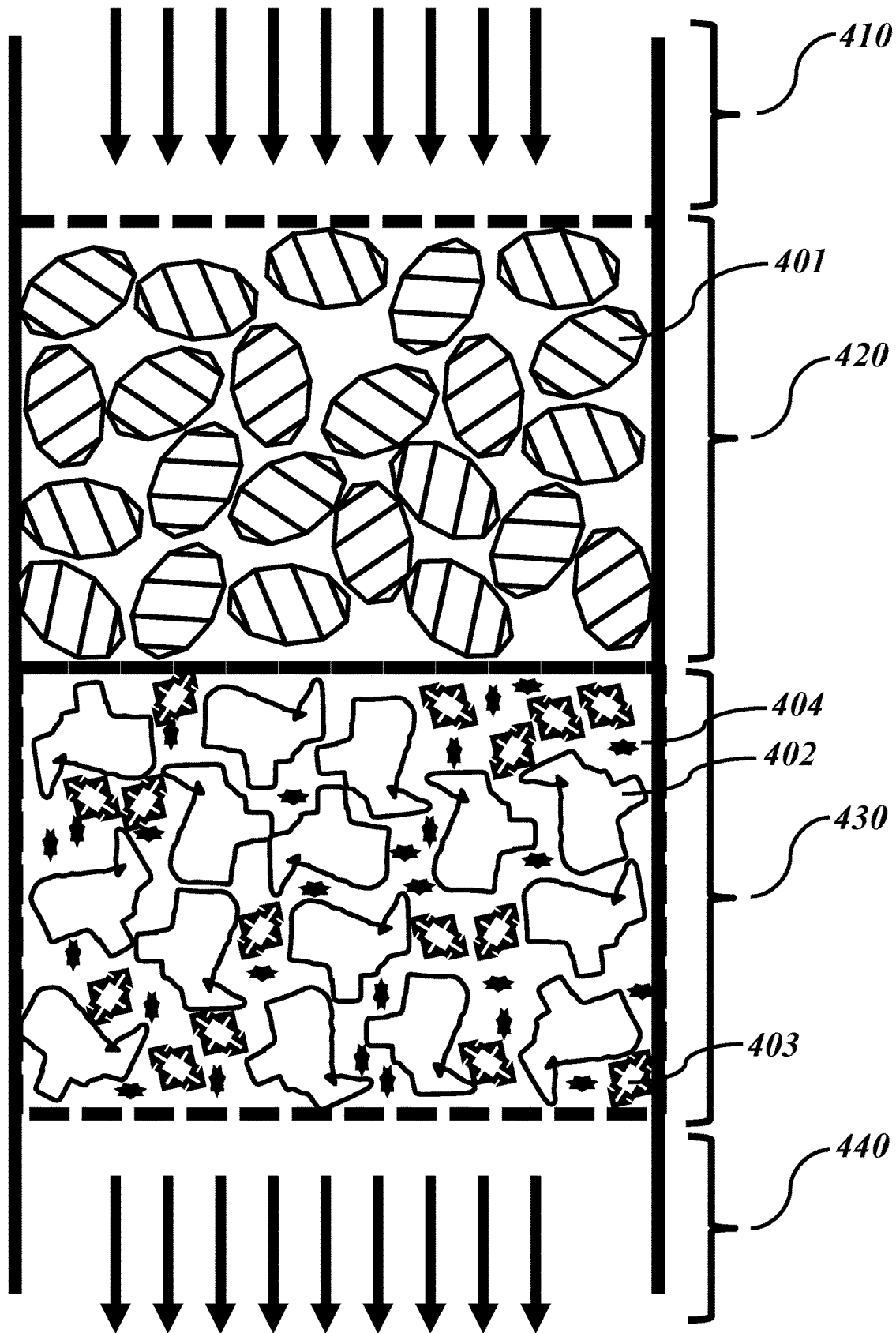
FIG. 4 depicts a system for fluid purification according to the invention, wherein the purification materials are provided within two successive zones.

FIG. 4 depicts a caricature of a non-limiting illustrative embodiment of a purification system according to the invention, as used in a pipe, tube, other channel structure, or drinking straw. In particular, it features in succession: a fluid influx zone 410; a CX-containing zone 420; a zone 430 containing other solids; and a fluid efflux zone 440 conveying purified fluid. The zones are separated by porous walls or porous media. Both zones 420 and 430 are porous to allow the flow of fluid, and one or both zones comprises sufficient polymer matrix to trap any chlorhexidine that dissolves into the fluid, however for ease in viewing, the polymeric matrix is not shown. The depicted particles are CX 401, a calcium phosphate compound CPC 402, sand 403, and activated carbon 404. Of the CPC, sand and carbon any one, two or three of them may be used—or none of them—without departing from the spirit of the invention.

Figure 5:
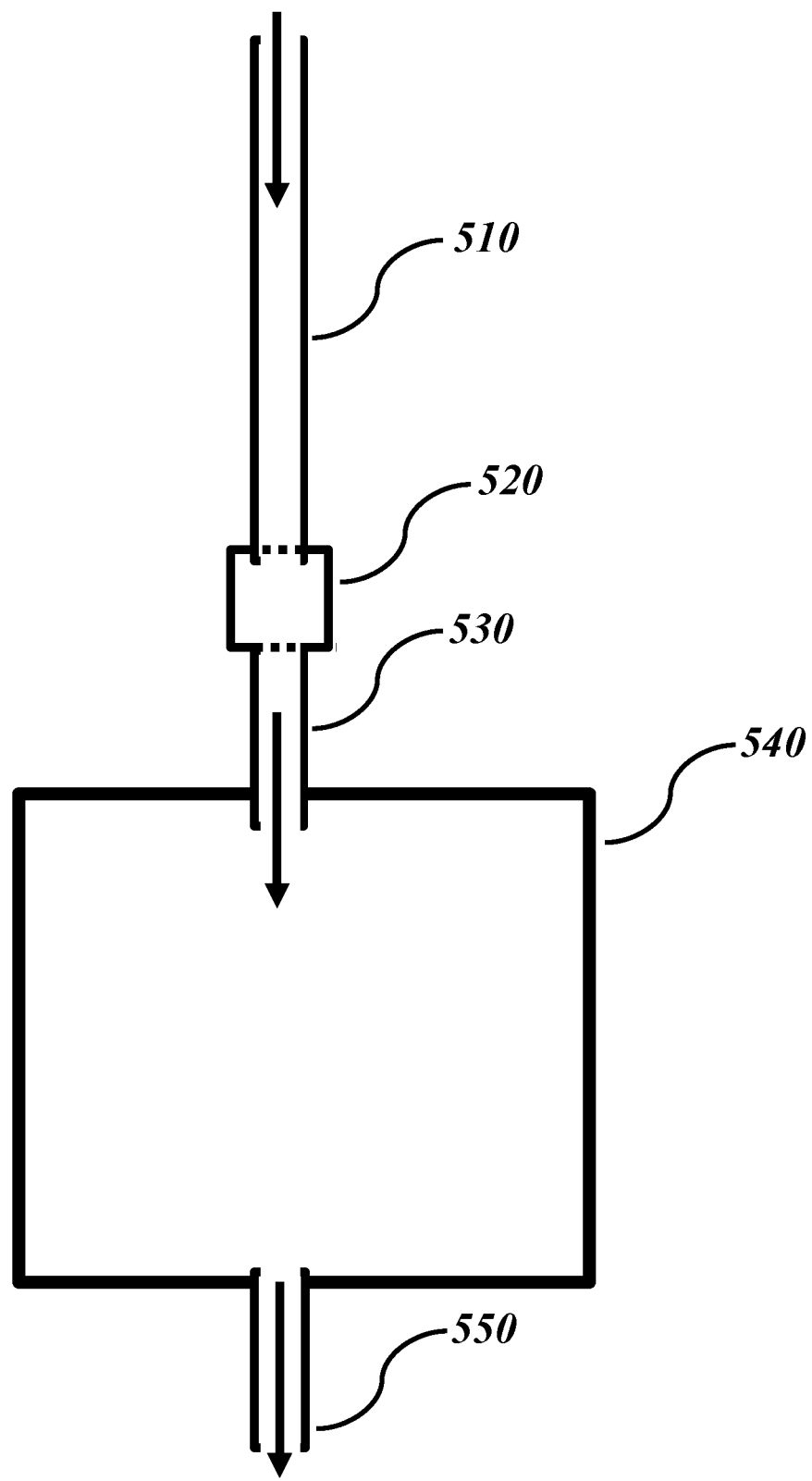
FIG. 5 depicts a system for fluid purification wherein the fluids are passed through a filter according to the invention before entering a structure for use.

FIG. 5 depicts a caricature of a non-limiting illustrative embodiment of a purification system according to the invention, e.g., as may be used applications within infrastructures. In particular FIG. 5 features in succession: a fluid influx zone 510; a treatment component 520 containing CX in a filter according to the invention, optionally supplied in the form of a replaceable cartridge within the housing of the purification device and wherein treatment component 520 has porous walls or porous media located at its inlet and outlet; an influx line 530 conveying the fluid purified at 520, a facility 540 such as a residence, office, production facility, hotel, hospital, cruise ship, water treatment plant or other facility; and an efflux channel 550 conveying waste water from the facility. In some embodiments some or all of the wastewater from 550 may be recycled by retreatment at 520.

Figure 6A:
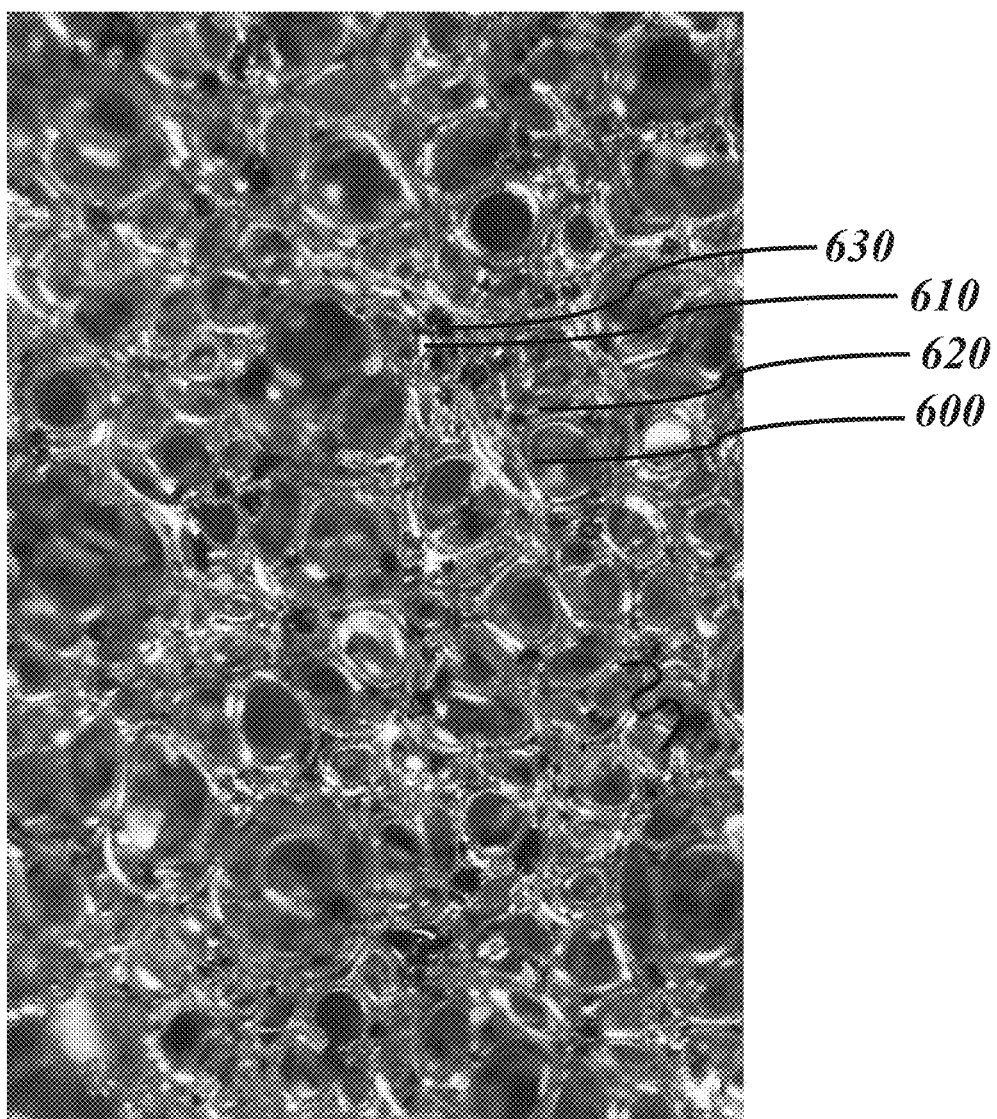
FIG. 6A is a low-magnitude micrograph of a polyurethane ether foam of the invention.
Figure 6B:
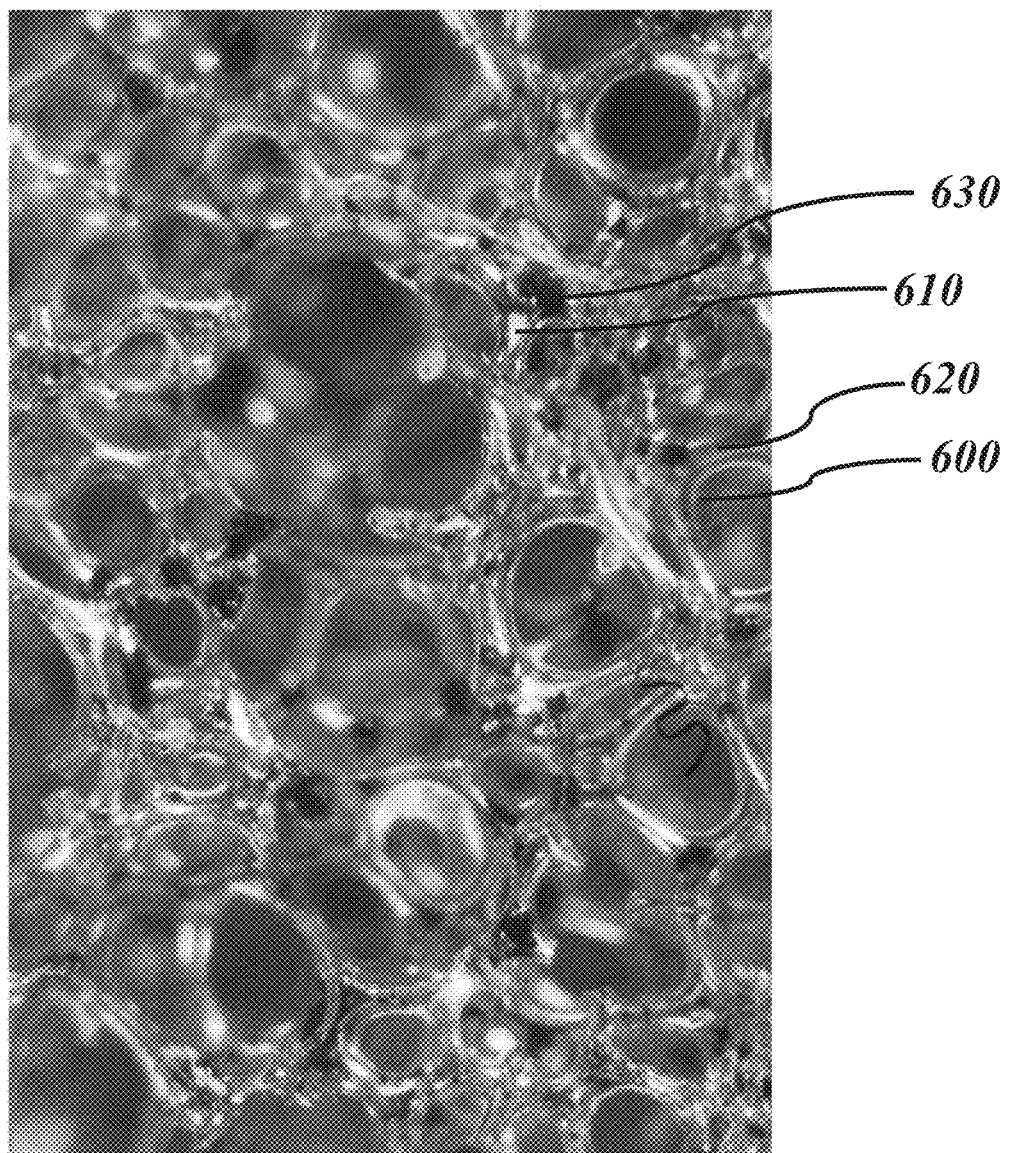
FIG. 6B is a mid-magnitude micrograph of a polyurethane ether foam of the invention.
Figure 6C:
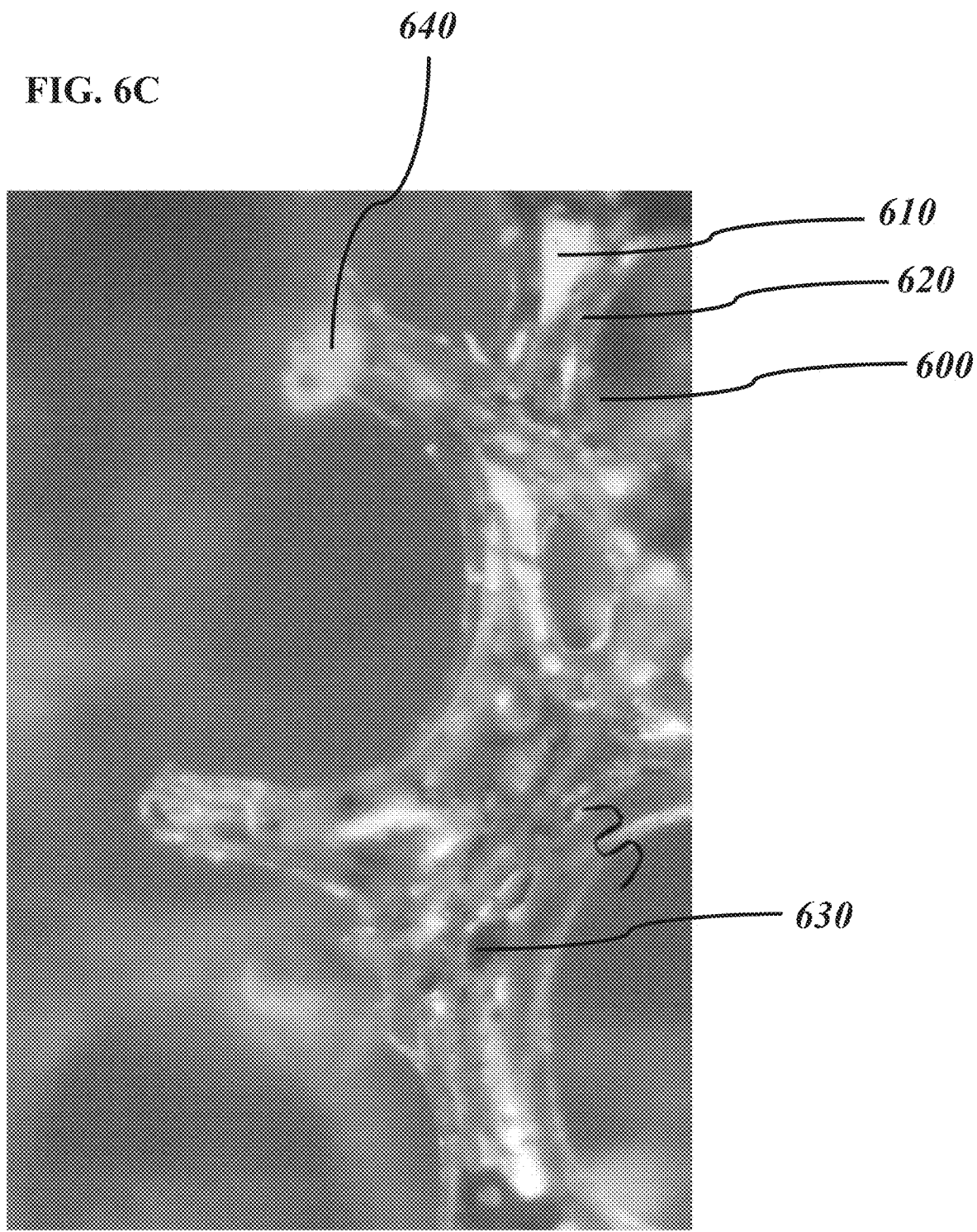
FIG. 6C is a high-magnitude micrograph of a polyurethane ether foam of the invention.

FIGS. 6A, 6B, and 6C depict micrographs of a polyurethane ether foam 600 according to the invention; within the three 6A shows it at the lowest magnification, 6B shows it an intermediate magnification, and 6C shows it at the highest magnification. White or yellowish particles of chlorhexidine 610 may be seen fully embedded within the translucent polymeric matrix 620. Black particles of carbon 630 are also embedded. In FIG. 6C broken strands 640 of the foam are visible, and caused by cutting or preparation of the foam for imaging.

Chlorhexidine

Normally fluids that contain even a small amount of chlorhexidine or its salts or hydrates have a bitter taste and or odor of the substance. The inventors have surprisingly discovered that chlorhexidine base in solid form, when combined with a larger polymeric mass, has no chlorhexidine taste or odor and release essentially no chlorhexidine into effluent yet retain potent microbicidal activity. The following description puts this into context.

Chlorhexidine base (CX) is N,N''''1,6-Hexanediylbis[N-(4-chlorophenyl) (imidodicarbonimidic diamide)]; its formula is $C_{22}H_{30}Cl_2N_{10}$ and its structure is shown below.

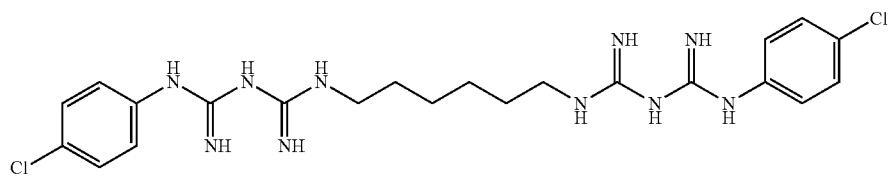 [SMILES: N=C(NCCCCCCNC(=N)NC(=N)Nc1ccc(Cl)cc1)NC(=N)Nc1ccc(Cl)cc1]

In aqueously dissolved form (here designated as DACX), the compound is a broad-spectrum biocide that kills both gram-positive and gram-negative bacteria, as well as fungi by a comparable mechanism, and also kills protozoa and compromises viral particles. DACX's salts and hydrates behave similarly. The activity of the dissolved naked base, DACX, illustrates this.

Uptake of DACX into bacterial cells is rapid, typically within 20 seconds. At low concentrations of DACX, their cell walls are compromised by electrostatic interactions, which can also have a bacteriostatic effect because it inhibits microbial adherence to surfaces and thus prevents formation of biofilms. At higher concentrations the cytoplasmic semi-permeable inner membrane is also damaged, resulting in leakage and cell death. At even higher aqueous concentrations of DACX the cytoplasm congeals or solidifies.

The biocidal activity of DACX is both broader and faster than for antibiotics, and in vitro it can kill virtually all gram-positive and gram-negative bacteria within 30 seconds. Because DACX destroys microbes from most pathogenic categories, the risk for developing opportunistic infections is low. DACX has also shown effectiveness against bacterial spores, protozoa, and enveloped viruses such as HSV, HIV, CMV, RSV influenza, and—in the presence of at least 70% ethanol—coronaviruses.

Because DACX binds to proteins, e.g., on skin, mucosa, mouth tissue and teeth, its activity persists there for long periods (e.g., ≥48 hours), yet unlike agents such as povidone-iodine its efficacy is not undermined by body fluids such as blood.

Although the biological properties of DACX are valuable, the chemical properties of CX hinder application development. It is poorly soluble in water (0.08%), yet even at such a low concentration it imparts a disagreeable bitter taste. The melting point of its crystals is high (134° C.), increasing the cost of thermal processing. And it becomes impermeable when formed into a filter, e.g. by sintering. In turn, that impermeability renders the filter properties moot. Still, even if the filter properties remained intact, the presence of CX in effluent would stiffen regulatory review and narrow the allowable uses for EPA registration and effluent management.

Moreover, despite its insolubility, the flow of fluids through CX-containing filters typically erodes CX and sweeps away microparticles. Any water purifier that allows such emissions must be registered with the EPA as a pesticide, as opposed to a purifier, moreover the maker and/or marketer of the filter becomes responsible for the ultimate fate and effects of the CX after it leaves the filter.

This combination of poor solubility in influent, detectable solubility in effluent, bitter taste, and erosion appears to have discouraged or prevented others from using CX for large-scale decontamination of potable liquids or breathable gases.

In an effort to mitigate the downsides of CX, less soluble derivatives have been made. U.S. Pat. No. 7,427,409 discloses synthesis of CX hydrates by base hydrolysis of the citrate salt. In that case the CX had 1.3 or 2.0 water molecules per chlorhexidine molecule, and was said to be amorphous material from which a permeable filter could be manufactured. The solubility was <0.04% under ambient conditions, rising to 0.089% at 90° C. Yet, although this addressed permeability, even at this lower solubility the implication of a dissolved CX substance left the effluent residue problem unresolved.

The present invention avoids the effluent residue. Again, without being bound by theory, this is believed to be because chlorhexidine is poorly soluble and highly localized in fluid about the solids, with adsorption onto polymer substrates removing essentially all of the substance from the fluid. Also, whereas small particles of chlorhexidine can be eroded or redispersed if loosely bound, this occurs to a much lesser extent if those are removed before the filter is employed.

The present inventors have determined that the following approximate ranges are useful for the weight percent of chlorhexidine present relative to its combination with the foam: 0.1% to 5%; 5-15%; 15-25%; 25-35%; 35-45%; 45-55%; 55-65%; 65-75%; 75-85%; and 85-95%; wherein each range is inclusive of its respective end values. In particularly useful embodiments the weight percent of chlorhexidine relative to its combined weight with the matrix is in the range: 0.1% to 95%; 0.5% to 85%; 1% to 70%; 2% to 55%; 3% to 40%; 4% to 25%; or 5% to 10%.

Binders

In certain embodiments a binder or adhesive is admixed with the CX. Depending on the nature of the particles and binder, binder can greatly improve filtration properties. For instance, in some particulate systems, a binder-free composition allows as much as 12% of E. Coli and 8% of poliovirus in an influent to pass through the filter mixture, apparently due to channeling caused by influent and effluent flow and by the exit of particles from the device, whereas exclusion is nearly complete when the filter's composite mixture has the form of a molded or extruded block held together by about 15 weight % of a thermoplastic binder. In some uses, a generous loading with binder doubles as a lubricant for shear flow of particles. See U.S. Pat. No. 6,180,016.

In certain embodiments the amount of binder is in one of the following ranges for the percent relative to the combined weight of particles and binder; 1-25%, 2-22%; 3-19%, 4-16%, 5-13%, 6-10%, or about 8%. In some embodiments the amount is in the range of 3-7 weight percent. In various embodiments the amount is in the range of 7-12 weight percent. In other embodiments the amount is in the range of 12-17 weight percent. In particular embodiments the amount is in the range of 17-22 weight percent.

Where the binder is swellable by liquid in the fluid, as little as 3% of binder by weight can be sufficient. Also, swollen binder is soft, imparting flexibility. The extent of swelling can be optimized by using a cross-linkable monomer, oligomer or polymer, because substantially cross-linked networks (such as hydrogels) have a maximum capacity. An additional benefit for ceiling values for a binder's absorption is that it can be prevented from expanding to seal pores; although the filter blend might remain permeable, the fluid's viscosity would rise and reduce permeation rates across a filter.

For robustness against extreme conditions relatively inert binders are useful, such as polyolefins, perfluoropolymers and polyethersulfones. Examples of sterilizing conditions include treatments with heat, steam, radiation (ultraviolet, infrared, microwave, and/or ionizing radiation), oxidants, reductants, formaldehyde, ethylene oxide or propylene oxide gases, beta-propiolactone, methyl bromide, reactive oxygen species, surfactants, metals, and electrochemistry. Where molding or extruding is desired, thermoplastic binders are particularly appropriate; polyolefins and nylons are non-limiting examples. Where biodegradable binders are desired, non-limiting examples include cellulose, starches, lignins, polyethylene oxides and polyethylene glycols, polylactic acids, polyvinylalcohols and their acetate esters, co-polylactideglycolides, and derivatives of any of those.

For an end user the most evident benefit of including a small amount of swellable binder in the mixture is that a powder can simply be poured into an empty filtration cartridge of any size or shape, and upon wetting for a short time the mixture will be ready for filtration service. This allows facile recycling of filter devices and avoids the need for specialized pre-molded or pre-extruded cartridge sheets and blocks.

Expandable Polymers

In certain other preferred embodiments the CX is admixed with an expandable substance such as a superabsorbent material or another material that swells when wetted. In some embodiments of the invention these may be binders. Superabsorbent polymers (also called SAPs or slush powder) absorb many times their weight in water due to hydrogen bonding: in some cases up to 500 times their weight of deionized and distilled water, and up to 50 times their weight of 0.9% saline solution. As the degree of cross-linking rises, the capacity and stickiness falls, but gel strength and shape retention are improved. Cellulosic materials absorb up to 11 times their weight in water, and lose most of it under moderate pressure. Starch grafted to acrylonitrile can absorb more than 400 times its weight; various grafts of acrylic acid, acrylamide and poly(vinyl alcohol) (PVA) are also used. Sodium polyacrylate is a particularly common SAP used today, as are acrylamide copolymers, ethylene maleic anhydride copolymers, and cross-linked carboxymethylcellulose. Persons of ordinary skill in the art are familiar with methods to make such polymers in various phases, including in gels (with photo-cross-linking), solutions and suspensions.

Upon the occurrence of wetting by fluid, the expandable substance may swell to bring the mixture into intimate contact with a membrane and the housing, and also prevents channeling, and further prevents CX particulates from exiting the device. A suitable modality is taught in South African patent document 2002/8316.

Foams

The present invention has found that it is particularly useful to deposit CX on or partly within porous matrices, such that fluids may flow through the foam and be disinfected by exposed CX solids there. Any foam may be used, such as a foamed metal or ceramic, but in particular foamed polymers are particularly useful. Experiments with various polyurethanes (Pus) have confirmed that linkers based on oligoesters are suitable for this purpose, and that linkers based on oligoethers such as oligo(tetramethylene oxide) [i.e., $—CH_2—CH_2—CH_2—CH_2—O—$] or oligo(dimethylene oxide) [i.e., $—CH_2—CH_2—O—$] are particularly suitable. Relative to most oligoester-linked PUs, oligoether-linked PUs tend to have: a stability advantage in humid and wet conditions; lower cost; softer, smoother surface texture; and spongier quality, enabling better throughput of fluids such as water or air.

As an example, CX crystals were able to be partially embedded during foaming of oligoether-linked PUs to produce a reticulated foam in a one-step process. Here the full range of FlexFoam iT!™ products from Smooth-On, Inc. were studied. FlexFoam iT!™ III foams were especially desirable due to the expansion volume (eV) of 14.1 mL/g and corresponding specific gravity (SG) of 0.071 g/mL The foams were made by dispersing CX crystals evenly in Part B of that two-part system; then part A (the "dope") was added and mixed to Part B: expansion of the foam carried the crystals in a uniform distribution throughout the foam. The uniformity was confirmed by substituting a yellow particulate pigment for CX. The vendor SuperSkinSystems, Inc. (SSS) provides similar polymer PU materials, with which 14.4 mL/g eV and 0.069 g/mL SG were obtained. The SSS materials provide scalable molding for a variety of shapes and volumes, yielding consistent expansion properties and even pore-size distribution. Smooth-On has a contact address at 5600 Lower Macungie Road, Macungie, Pa. 18062, and order desk at (610) 252-5800. SuperSkinSystems, Inc. has a contact address at 100 Petty Road, Suite C, Lawrenceville, Ga. 30043, and technical desk at (404) 216-4711.

Although the foams can be effective with 5% by weight or less of CX solids, we have made them readily with up to 9% by weight and contemplate that substantially higher proportions of CX solids can be used also. Particularly useful ranges by weight percent for encapsulation of CX solids in foam include: 0.5 to 10.0; 1.0 to 9.0; 2.0 to 8.0; 3.0 to 7.0; 4.0 to 6.0; or about 5.0 weight percent, but the invention is not so limited.

Hygroscopic Substances

Inclusion of hygroscopic substances can retain water from the fluid (whether the fluid is aqueous, air, or another medium) in close proximity to the CX to facilitate microbicidal action. Such substances are preferably essentially insoluble in water or any other fluid medium that is employed, in order to avoid being leached. For instance, they may be cross-linked sulfonium-derivatized polymers.

Parameters and Utility

Composition and Proportions. Naturally the amount of CX substance and the relative amounts of polymer and other materials depend upon the throughput volume needed and the specifications for time to replacement or regeneration of the purification media. A typical specification for a water purification cartridge is that relative to the throughput volume of water the cartridge contains enough material to provide ≥6-12 months of service from the cartridge when in use for water purification. These may comprise regeneratable materials or be disposable.

Porosity and Permeability. As is well-known to persons of ordinary skill in the design of filtration compositions for fluids, the pore size and physical dimensions of the purification particles may be manipulated for different applications, and variations in these variables will alter flow rates, back-pressure, and the level of microbiological contaminant removal. Compositions having a permeability of at least 100 millidarcys allow the passage of a fluid. In particular, with respect to embodiments of mixed particulate compositions according to the invention for the filtration of water, such embodiments have a permeability of at least 100 millidarcys, at least 1,000 millidarcys, at least 10,000 millidarcys, at least 100,000 millidarcys, or at least 1,000,000 millidarcys; millidarcys are described in the definitions section of this application. Purification materials having pore sizes in the range of 200-800 microns in diameter are particularly useful according to the invention for the flow of fluids through the purification media, but the invention is not so limited.

Adsorption. Adsorption occurs by different mechanisms, but in general Chemisorption deposits a monolayer of molecules on the surface by relatively strong attractions, for instance by the root mean square of dispersion forces, polar forces, and hydrogen bonds comparable to solubility parameters, whereas physisorption may deposit multilayers by van der Waal's forces. See, e.g., D. Jones et al., Int. J. Pharm., 114:257-261 (1995), noting the correlation between the release rate of chlorhexidine from ethycellulose films as a function of (distance between) their relative solubility parameters; see also N. Hiraishi et al., Dental Materials, 24(1):1391-1399 (2008), noting the correlation between material hydrophilicity and chlorhexidine retention rate. In general it is practical to confirm that polymer adsorption fully offsets release of chlorhexidine into fluid for the necessary filter capacity by measuring the amount of polymer necessary to reduce the chlorhexidine concentration to a level where it is odorless, tasteless, not present at more than 3 mg/L, and sustainable for the duration of a specified filter concentration, such as for example, for at least 800 gallons per cubic inch of foam media in a filter cartridge.

Devices

The device adaptability of the invention compositions is unusually broad for the relevant art. The microbicidal system may be provided as filter disks, for use in any filter device contours without reliance upon a molded filter cartridge from an original equipment manufacturer. Thus existing filters from most sources can be retrofitted readily and inexpensively. This is particularly important where pure water must be available at a low price, as in food and drug manufacturing and also for third world consumers. The invention also enables comprehensive purification by a single filter module. In particularly useful embodiments the purification mixture is placed in a module within a drinking straw. Likewise, mixture may be used to create an essentially instant purification cartridge in a water supply for a residence, office, production facility, hotel, hospital, cruise ship or water treatment plant.

Example 1

Ester-Based Polyurethane Foams

Reticulated ester-based open-cell polyurethane foam disks were obtained from Foamulations, LLC, 303 Najoles Rd., Suite 112, Millersville, Md. 21108. These are called cartridge disks, and here were fitted into cylindrical cartridge sumps. The disks had diameters of 68 to 71 mm, or about 70 mm (2¾ inches); with a thickness of 19+1 mm (about ¾ inch), representing about 41.8 cu. cm (about 2.55 cu. in.) of volume per disk Their weights after washing were in the range 4.5 to 7.4 grams, but on average about 5.5 grams. Their estimated use life is 1,500,000 gallons/cu. ft. (ca. 868 gallons/cu. in.). The cartridge housings were 10 inches long and had internal diameters of ca. 2 $^{11}\!/_{16}$ inches. A stack of 11 disks was placed inside (~8¼ inches deep). Disks of this type were prepared containing from 0% to 9% by weight of CX.

This supplier has its own proprietary method to produce the foam, but in general any foam formed from a suitable polymer may be used, for instance a non-limiting illustrative method is: (1) production in advance as a closed-cell polymer foam; (2) etching or fire-blasting to open the cells; and (3) cutting to the final shape. Polyurethanes are a particularly useful class of materials for this purpose, but other polymers may be used such as polyethylene, polypropylene, polybutadiene, polyisoprene, cellulose, cellulose derivatives, etc.

Chlorhexidine base (CX, CAS no. 55-56-1) was obtained from Medichem S.A., Fructuós Gelabert, 6-8, 08970 Sant Joan Despi, Barcelona, Spain. The powder is white or slightly off-white and matches the standard IR spectrum, and is clear and colorless—or nearly colorless—when dissolved. The specification is <500 ppm (0.05%) chloroaniline, <1.0% loss on drying, and ≤0.1% sulfated ash. The solids are rhombohedral crystals or other shapes; the average particle is 5 microns long and 1-2 microns wide, and they are fairly uniform in size. In particularly preferred embodiments the crystal have an average length of from 1-10 microns and an average aspect ratio relative to the width of from 2:1 to 10:1, however the invention is not so limited. In another particularly preferred embodiment the average width of CX particles is no greater than the average pore diameter of the porous polymer matrix, however the invention is not so limited.

The vendor Foamulations affixed that CX powder to the interior of the foam, such that the final foam was ca. 50% chlorhexidine by weight, i.e., 1:1 versus polyurethane by weight. The loading rate is variable, such that the chlorhexidine:polyurethane ratio can range from 0.4:1 to 1.3:1. In a particular run, 0.81 g CX powder and 0.09 g tricalciumphosphate [$Ca_3(PO_4)_2$] were infused per cubic inch of foam. This supplier has its own proprietary method to adhere substances to the foam's interior but in general any foam using suitable affixing means may be used, for instance a non-limiting illustrative example is where the foam is: (1) evacuated to suck glue into the interior (e.g., where cyanoacrylate monomer is provided as a gas and polymerizes on the interior); (2) dried to set the glue in whole or in part; (3) re-evacuated; and (4) supplied with fines of CX and optionally other compositions while still evacuated, to adhere them to foam interior surfaces. The CX proportions are relatively high in this foam, but the inventors have found that CX loadings can be reduced to <0.1:1 versus foam polymer by weight.

The chlorhexidine-loaded reticulated foam disks as obtained from the vendor in this example left a very bitter taste in effluent water that was exposed to them. The source of the flavor was identified as loose chlorhexidine particles and 3- and 4-chloroaniline. With experimentation, the problem was eliminated by washing with 120-140° F. (49-60° C.) municipal tap water until the taste was eliminated as perceived organoleptically, according to a consensus test. Washings reduced the weight percent of CX in the foams from ca. 68-72% to ca. 60-63%

HPLC testing of the effluent by Materials Analytical Services (MAS) in Johns Creek, Ga., found no detectable chlorhexidine or 2-, 3-, or 4-chloroaniline. The method's lower limit of detection for chlorhexidine was 68 micrograms/L and 2.8 milligrams/L in separate tests. The lower limit of detection for the chloroaniline isomers was 60 micrograms/L for each of 2- and 3-chloroaniline, and 57 micrograms/L for 4-chloroaniline.

Two cartridges of filters were tested: 11×7 cm thick disks (unit A), and 4×4.3 cm thick disks (unit B), respectively. The microbicidal activity was tested against *E. coli* by Biological Consulting Services of North Florida, Inc. (BCS) in Gainesville, Fla. For an influent having $4.1 \times 10^7$ cfu/100 mL, the effluent had a >6.6 log reduction and 4.9 log reduction in live cells for units A and B respectively, based on collection of the first five 1-liter aliquots of effluent from each cartridge.

These foams are protected within cartridge housings. However, it was found that after a month in water these particular polyesters tended to crumble when handled. This instability was evidence of hydrolysis, and was not seen in the polyether foams.

Another observation was that preparation of polyurethane ester foams in the common closed-cell format may inevitably require several steps and complex equipment over a period of days to obtain the necessary matrix. The process is not clean, and also requires attention to chemical safety.

Example 2

Oligoether-Based Polyurethane Foams in 10-Inch Cylinders

Reticulated ether-based open-cell polyether foam disks were obtained for the same type of 10-inch cartridge housing described in Example 1. In this case the foams were obtained in one step as reticulated open-cell foam cylinders with a diameter of 2⅝ inches and a height of 8½ inches for a single component. The diameter of these foam units was slightly compressed during insertion into the housing, providing a snug fit.

These oligoether-based polyurethane foams had expansion volumes in the range of 7.8 to 14.1 $cm^3$/gram, corresponding to specific gravities of 0.128 to 0.071 gram/$cm^3$, respectively. The product FlexFoam iT!™ III was particularly useful in this respect but the invention is not so limited. FlexFoam iT!™ is a product of Smooth-On, Inc., whose address is 5600 Lower Macungie Road, Macungie, Pa. 18062 and phone number is (610) 252-5800.

FlexFoam iT!™ uses a two-part system. CX crystals were added to Part B. Then Part A, the "dope" was added and mixed. The expanding foam carried the crystals in an even distribution. The uniformity was confirmed by substituting yellow pigment particles for CX, obtaining an even dispersion throughout the foam. Foams with similar properties and utility are available from SuperSkinSystem, Inc. (SSSI), whose address is 100 Petty Road, Suite C, Lawrenceville, Ga. 30043 and whose phone number is (404) 216-4711. FlexFoam iT! III and SSSI foams have been prepared in this cartridge format, and as shown below also in cylinder format for showerheads and in short-cylinder format. Units of these types were prepared containing from 0% to 9% of CX by weight.

These polyurethane ether foams were also much more water-stable than polyurethane ester foams obtained in Example 1. And their ability to be blown within molds or cartridge housings allowed them to be created easily in a variety of dimensions and shapes in a clean, precise, rapid, flexible, efficient, and environmentally friendly manner.

Micrographs of these foams show that virtually all of the CX crystals can be entirely submerged within the polymer that makes up the foam. That is, the crystals are fully encapsulated or embedded within the walls of the pores. Surprisingly, these foams had superior microbicidal performance over the ester-based polyurethane foams for which crystals lay adhered to the surface in their pores. Thus with 5% CX content as measured by dry weight, there were 9-log reductions in microbial content, to zero viable cells. By contrast, even with 50% CX by dry weight the Example 1 materials yielded only about 3- to 6-log reductions, moreover some live bacteria survived.

Without being bound by theory, it is doubtful that microbial cells can diffuse into the bulk polymer to any significant degree, thus it is believed that CX diffuses through the ether-based polyurethane to the pore surface and into the aqueous media, and that the polymeric surface of the pores also interacts directly with the pathogen cell walls or envelope. However, the invention is not so limited, and again it is not bound by theory.

It is also believed that macropores in the matrix allow cells to pass through, whereas nanopores allow only the carrier (e.g., aqueous media) to pass through, however the invention is not so limited.

Example 3

Oligoether-Based Polyurethane Foams in Showerheads

Reticulated ester-based open-cell polyether foam cylinders were prepared as shown in Example 2, for use in a showerhead having a hollow cylindrical housing 4½ inches long and 2½ inches wide. Foam units were obtained in one step with a diameter of 2¾ inches and a height of 3 inches. The diameter of these foam units was slightly compressed during insertion into the housing, providing a snug fit for a tube with a 2½-inch inner diameter.

Example 4

Oligoether-Based Polyurethane Foams in Short Cylinders

Reticulated ester-based open-cell polyether foam cylinders were obtained as shown in Example 2, for use in a water purification cartridge from Pudow having a hollow cylindrical housing 1½ inches wide. Foam units were obtained in one step with a diameter of 1 9/16 inches and a height of 3½ inches. The diameter of these foam units was slightly compressed during insertion into a corresponding housing, providing a snug fit for a tube with a 1½-inch inner diameter.

Example 5

Chemical Leaching and Byproduct Data

In some third-party reports, chlorhexidine has a solubility of ca. 80 mg/100 mL in water at ambient temperature, or about 0.08% by weight. Human taste and smell are able to detect the presence of many compounds when present even at parts per billion, and CX has a bitter taste and displeasing odor in addition to very low regulatory limits on its presence in potable water and environmentally released water. Thus, it was important to ensure that the invention left essentially no CX in effluent from filters of the invention. In addition, 2-, 3-, and or 4-chloroaniline (CA) are important impurities in CX that must be avoided or removed before end-users are exposed to water that is filtered according to the present invention. Testing had suggested that 1.2-3.0% of CA by weight is present in CX by weight, as measured by gas chromatography-mass spectrometry in headspace gases. The loose CX and CA impurities were removed by washing, as discussed elsewhere herein.

Leaching of chlorhexidine from filters of the present invention was evaluated using a Shimadzu Prominence High Performance Liquid Chromatograph (HPLC) with a Synergi Hydro-reverse phase 4p C18 column maintained at constant temperature (that temperature, 140° F. (60° C.), common in home, office, hospital, and hotel hot water systems, including for showerheads). The HPLC mobile phase was 40% acetonitrile (ACN, 60% water, with 0.05% trifluoroacetic acid (TFA), 0.05% heptafluorobutyric acid (HFBA), and 0.1% trimethylamine (TMA), with a flow rate of 1.0 mL/min. Injection volumes were 25 microliters (μL) each, with UV detection at 270 nm for CX and 254 nm for CA isomers. Analysis screened for concentrations of chlorhexidine (CX) and 4-chloroaniline, 3-chloroaniline, and 2-chloroaniline (4-, 3-, and 2-CA) using commercial standards from Sigma-Aldrich. Detectable levels of those compounds were in mg/L (ppm): 0.069 for CX, 0.086 for 4-CA, 0,072 for 3-CA, and 0.073 for 2-CA. The tested foam was from Example 1 above.

A study with a control—meaning water without use of a filter—found that under standard aqueous conditions chlorhexidine reaches near-equilibrium saturation levels within 30 seconds of introduction of 50 mg CX to 1 L water at 140° F. with stirring. The amount of added CX was twice the expected amount needed to reach saturation. The final concentration of CX was 0.82 mg/L (ppm) at 20 minutes, and no isomer of CA was detectable.

The tested filtration pads contained 5% activated carbon by weight; the carbon consisted of kilned rice husks with an ionic binder; this composition is capable of removing lead (Pb), mercury (Hg), and butadiene monomer, among other potential contaminants. The pads further contained 5% CX by weight. The pad was porous, mainly comprising an open-cell polyurethane foam based on condensation of isocyanate and polyether (i.e., oligoethylene oxide). The solids in the foam were finely ground (35 mesh). The pads had a 4-inch diameter, and were stacked to a 8.5-inch height.

Following manufacture, the pads were rinsed with municipal water held at 110-120° F. to remove any unbound CX. Effluent from the first 0.1 gallon of rinse water contained 0.089 mg/L of CX and no detectable CA isomers. The next 9.9 gallons of rinse water contained no detectable CX or CA isomers.

Example 6

Chlorhexidine Dissolution Data

For chlorhexidine in its basic form, i.e., without the presence of acids, the published data on saturation levels in water vary widely, with reported values of 10, 26, 61 and even 800 mg/L (ppm) when measured at ambient temperature. Moreover, it is well known that hot water dissolves small molecules to a greater degree than does water at room temperature, because of the greater energy in heat. To test the expected lifetime of CX crystals in the present invention, six 50 mg aliquots of pure CX powder were exposed to 1 liter each of 140° F. (60° C.) municipal water for respective time periods of 0 seconds, 10 seconds, 30 seconds, 90 seconds, 300 seconds, and 1,200 seconds, then the remaining solid CX was removed and the CX concentration in the water was determined. The system was found to approach a 1 mg/L saturation level of CX within the first 10 seconds of exposure to the hot water. This represented just under 2 weight percent of the powder in each case, and no more than that dissolved even with 20 minutes of exposure.

No chloroani line impurities were detectable in the water. This is believed to be because (a) the chloroaniline content of the residual solid CX was still trapped there, and (b) the chloroaniline content of CX that dissolved into the hot water evaporated during the time trials and the sampling.

In the foams of the invention much of each crystal surface is not directly exposed to the aqueous medium. Hot-water tests of that system find that CX is undetectable in the effluent, meaning that there is at most ca. 70 µg/L (70 ppb) of dissolved CX. This is a surprising finding: the same foams remain potently microbicidal even though CX cannot be detected in their effluent by the standard analytical methods.

Example 7

Preliminary Data for *Legionella pneumophilia* Serotype 1 (Lp1)

CX CONTROL: The disinfectant efficacy of free-standing exposed CX surfaces in water was tested by a third-party pathogen laboratory by placing a dose of either 4.5 g, 9 g, or 12 g of solid CX into respective 800-mL volumes of water containing ~$9\times10^6$ colony-forming units (CFU) of Lp1 per mL. The microbial liquids were prepared from the same 3.5-liter 3.0 McFarland suspension. The introduction of CX was done with stirring, and 1-mL samples were taken at intervals of 30, 45, 60, 90, and 120 seconds. Each sample was then added to 9 mL DE broth, which neutralized and terminated the antiseptic activity of CX; then the samples were serially diluted and plated to triplicate BCYE plates for viability counts. The 4.5-g CX run reduced the cell count by log ~0.3 over the first 30 seconds. The 12-g CX run reduced the cell count by log ~4.8 over the course of the 2-minute reaction period. Thus, even at the low concentrations of dissolved CX, this suggested that an inline two-module system is viable: the first for reaction of CX, and the second for adsorbing or absorbing any CX that dissolves. The tested foam was from Example 1 above.

FOAM TRIAL: The disinfectant efficacy of CX partially embedded in reticulated polyurethane foam was tested by ambient pressure (i.e., gravity-driven feed at low influent and filter height) through foam disks with 2.5-inch diameter and 1-inch thickness. Lp1 bacteria were suspended and dispersed in 10 L deionized (DI) water with a cell count of $3.12\times10^7$ CFU/mL. For each experiment, the filter was pre-wetted with DI water and then 1 L of the suspension was gravity-fed through a single filter housing that contained either the control (reticulated foam disks with no CX) or the test pads (reticulated foam disks with embedded CX). Then 4×0.5 L aliquots were collected from the effluent in each experiment. These aliquots were then sampled, plated, and grown in triplicate on BCYE plates. For the control, the first three aliquots contained nearly the same concentration of live cells as the influent held (all $\geq6\times10^6$ CFU/mL). For the test run, the log reduction was 1.58; collected aliquots had ~2.6% of live cells relative to the influent cell count, or 97.4% reduction. Thus, a stack of filter pads in a cartridge as shown in EXAMPLE 1 was used in subsequent experiments to achieve essentially complete eradication of bacterial cells.

Example 8

Hot Water Tank for *Legionella pneumophilia* Serotype 1 (Lp1)

A model system was used to simulate growth conditions in large building hot water tanks, to measure the efficacy of the present invention against the environmental full range of *L. pneumophilia* bacteria—not just the Lp1 strain—and also to test it against a mix of Heterotrophic Plate Count bacteria (HPC bacteria).

The model system consisted of three 19-gallon electric hot water tanks, each with its own respective hot water loop and Watts model 500800 recirculating pump. A manifold combined the returns from each loop and distributed water back to each tank. The system had been constructed of typical materials for building water systems, including copper and PEX piping. The water volume in the combined system was about 60 gallons. The typical system pressure was in the range of 30-40 psi. The operating temperature was in the range of 100-110° F. (37.8-43.3° C.). The flow rate was 1.2-1.5 gallons per minute (GPM). The system was inoculated with environmental *L. pneumophilia*, that is, not only Lp1 but also other *L. pneumophilia* strains as well as other associated HPC bacteria. The environmental inoculum was about 5 L containing over 3,000 CFU/mL. The system was maintained and monitored multiple times per week for 8 weeks after inoculation, including sampling and testing for populations of Lp and HPC.

On the day of evaluation, the system was spiked with a suspension of Lp that had been recovered and grown from a previous sampling, to nominal $10^6$ CFU/mL. This served as the control.

In separate runs, control (meaning filter cartridges like the invention but not containing CX), and test modules (meaning filter cartridges of the invention prepared according to EXAMPLE 1 herein) were mounted inline in the model system's recirculation loops. Then at the end of each run, before sampling about 3.5 L of outflow was drawn off and discarded to remove the system's residual pocket of cold water, then for each run six successive samples of 750 mL were collected. Similar methodology was used to spike with and test for HPC, with initial nominal $10^5$ CFU/mL.

The control and test samples were evaluated for Lp on selective agar plate medium, BCYE with glycine, vancomycin, Polymixin B, and cycloheximide (GVPC) to inhibit any HPC that might interfere with Lp growth. Colonies of viable Lp were counted after six days of incubation; the counts were based on a triplicate plate set for each sample, with results averaged to calculate CFU/mL.

LP TESTING: The control populations of Lp (meaning those not exposed to CX) were in the range of $5.30 \times 10^4$ to $1.67 \times 10^5$ CFU/mL. The populations in runs that employed the present invention had 100% elimination of live Lp bacteria. On the basis of reducing CFU/mL to less than 1 (i.e., to zero), this represented log reductions in the range of 4.72 to 5.22. Note that these are not the upper limit of efficacy, because the maximum was not evident at these CFU/mL counts.

HPC TESTING: The control populations of HPC (meaning those not exposed to CX) were in the range of $1.90 \times 10^3$ to $8.27 \times 10^3$ CFU/mL. The populations in runs that employed the present invention had 100% elimination of live HPC bacteria. On the basis of reducing CFU/mL to less than 1 (i.e., to zero), this represented log reductions in the range of 3.28 to 3.92. Note that these are not the upper limit of efficacy, because the maximum was not evident at these CFU/mL counts.

HPC testing employed the pour plate method in R2A medium, with incubation for five days prior to counting colonies.

Example 9

Effect of Pre-Washing Foams on *E. Coli* Elimination

Washing is used to remove all traces of loose CX and any soluble CA from the system, to improve safety for end users and to remove filter-based artifacts of taste and smell from filtered water. Here the filter pads were conditioned before testing by a 2-liter flush with general test water that was free of cells. The flow rate through the filter was 3.0 L/min. The filter housing had a 2.5-inch inner diameter and 10-inch inner length as in EXAMPLE 1 above A third-party laboratory tested the efficacy of these pre-washed filter pads against *Escherichia coli* (*E. coli*) bacteria. There the filter cartridge was connected to a pressure vessel containing General Test Water #1 (GTW1, NSF P231). This water had a pH of 8.0, turbidity of 0.1 NTU, 0.5 ppm total organic content, total dissolved solids (TDS) of 188.0 ppm, and hardness of 1237.0 ppm. This water was passed through the cartridges in five discrete samples pressures for which the pressures were respectively 1 psi, 2 psi, 3 psi, 4 psi, and 5 psi at a flow rate of 3.0 L/min. and a temperature of 40.7° C. (ambient was 26.5° C.). The influent concentration of *E. Coli* was $4.1 \times 10^7$ CFU/100 mL, i.e., $4.1 \times 10^5$ CFU/mL. The pressures had no discernitble effect on the efficacy, in that the system eliminated over 99.99998% of the live bacteria, i.e., no detectable growth, and greater than log 6.6 reduction in each case.

Example 10

High-Log Data for *E. Coli* Elimination

TEST CONDITIONS: The effectiveness of filtration pads that had been made according to the invention was evaluated by a third-party commercial laboratory as follows for killing and removal of *Escherischia coli* bacteria, which provides a reliable stand-in for a variety of other pathogens in addition to itself. The test used $4.3 \times 10^8$ CFU/L for cell counts for influent. The influent water was provided with constant flow under near-ambient pressure (1 p.s.i.), at 40.5° C. (104.9° F.; cf. ambient temperature was 26.3° C.), pH 8.0, 0.3 nephelometric turbidity units (NTU) turbidity, 0.4 ppm total organic content (TOC), 184.3 ppm total dissolved solids (TDS) 129.0 ppm water hardness, 0.0 ppm total chlorine, no polyphosphate. All instruments had been calibrated or validated with NIST traceable standards. The filter pad was conditioned before testing by a 2-liter flush with general test water; the test water was free of cells. The flow rate through the filter was 3.0 L/min. The filter housing had a 2.5-inch inner diameter and 10-inch inner length as in EXAMPLE 1 above. Effluent was collected in five 1-liter aliquots and tested.

CX-FREE FOAM CONTROL: For a CX-free filter, reduction of viable cells was about 94% (94.4, 93.9, 93.6, 94.7, and 94.6%) for all five aliquots of effluent.

TRIAL: For a filter according to the present invention, the number of viable cells were reduced by a factor of over $10^{8.6}$, i.e., over 99.9999998% of the cells were killed, in all five aliquots of effluent. The effluent was tested by introduction of 100 CFU/mL of *E. Coli*, and found to have essentially no activity against the bacteria, i.e., the effluent contained no microbially detectable active ingredient (CX).

Embodiments of the invention described herein are illustrative and not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:
1. A microbicidal filtration system comprising:
 a) a set of solid chlorhexidine (CX) particles having the following characteristics:
  i) a purity of at least 97.0% chlorhexidine by weight, when any presence of counterions or water molecules is factored out; and
  ii) no more than 3.0% by weight of chloroaniline impurities, when any presence of counterions or water molecules is factored out;
  iii) the CX particles are each characterized in having a releasing surface from which molecular chlorhexidine may dissolve into an aqueous medium that passes over said CX particles or dissolve into a polymer matrix that is juxtaposed at that surface;
  iv) a particle phase composition selected from the group consisting of amorphous, crystalline, and mixed amorphous and crystalline, wherein the phase composition of each particle is the same as or independent of the phase composition of a majority of other CX particles in the set;
 b) a porous matrix having the following characteristics:
  i) when any presence of chlorhexidine and of chloroaniline impurities is factored out, at least 90% of the matrix by weight is constituted by one or more polymers that do not dissolve in water;
  ii) the porous matrix has exposed polymer surfaces that are capable of trapping chlorhexidine from an aqueous fluid in which the chlorhexidine is dissolved; and
  iii) the matrix has a permeability of at least 100 millidarcies relative to water;
 c) disposal of the CX particles and porous matrix in a relative manner to form a microbicidal filter wherein:
  i) the chlorhexidine particles are permanently affixed to the porous matrix;

ii) the affixed chlorhexidine particles comprise from 0.5% to 95% of the combined weight of the porous matrix and the chlorhexidine particles affixed thereto;

iii) when the fluid is aqueous, release of dissolved chlorhexidine from the microbicidal filter into a flow of aqueous fluid is essentially fully counterbalanced by trapping of dissolved chlorhexidine at the exposed polymer surfaces in the porous matrix, such that when said fluid flow at a rate of 0.3 to 1.3 liter/(minute*square inch) through the microbicidal filter, wherein:

A) effluent from the filtered fluid flow is free of any detectable taste and odor of chlorhexidine;

B) dissolved chlorhexidine, if present in the effluent, is present at less than 3.00 milligrams per liter of effluent;

C) each of 2-, 3-, or 4-chloroaniline, if present in the effluent, is present at less than 0.100 milligrams per liter of effluent; and D) such full counterbalancing is sustainable for a throughput volume of at least 800 gallons of water at room temperature per cubic inch of foam in a microbicidal filter; and d) microbicidal capacity such that, within the sustainable throughput volume at the rate of aqueous flow shown in (c)(iii)(D), the filter kills or otherwise inactivates pathogens from an influent, such that at a minimum the reduction of live cells between influent and effluent occurs to a degree selected from the group consisting of the following:

i) a 6.6-log reduction in coliform bacteria *Escherichia coli* or *Klebsiella terrigena* for samples having $1\times10^7$ live cells/100 mL influent;

ii) a 4-log reduction in a Coronavirus strain or process resistant viruses poliovirus 1 (LSc) or rotavirus (Wa or SA-11) for samples having $1\times10^7$ viral particles/L influent;

iii) a 3-log reduction in cysts of *Giardia muris* or *Giardia lamblia*, for samples having a concentration in the range of $1\times10^6$ to $1\times10^7$ organisms/L influent; and iv) a 3.8 log reduction in a *Legionella* bacterial strain for samples having $6\times10^3$ live cells/L influent.

2. The system of claim 1 wherein the water-insoluble polymer(s) is or are selected from the group consisting of: polyurethanes; polyolefins; polyesters; polycarbonates; synthetic and natural polyamides; polyimides; polyacrylates; polymethacrylates; vinyl polymers; rubbers; polyacrylonitrile; polysiloxanes; polysaccharides; and combinations and blends thereof.

3. The system of claim 1 wherein the water-insoluble polymer(s) has or have a melting transition temperature greater than 57° C.

4. The system of claim 1 wherein the fluid is selected from the group consisting of: water; ethanol; isopropanol; bodily fluids; medications; air; oxygen gas; nitrogen gas; carbon dioxide; argon gas; nitrous oxide; an anesthetic gas other than nitrous oxide; and mixtures thereof.

5. The system of claim 1 wherein the influent is an aqueous medium selected from the group consisting of: potable water; a beverage; a stream for transfusion of bodily fluids; an aqueous solution for use in a medical procedure; a recycle stream in a chemical process; a recycle stream in a cell culturing process; and mixtures thereof.

6. The system of claim 1 wherein the fluid is air that has an average relative humidity selected from the group consisting of at least: 20%; 25%: 30%: 35%: 40%: 45%: 50%: 55%: 60%: 65%: 70%: 75%: 80%; 85%; 90%; 95%; and 100%.

7. The system of claim 1, wherein the porous matrix has a form selected from the group consisting of: an open foam; a reticulated foam; a fiber mat; a knitted fabric; a woven fabric; a nonwoven fabric; a material formed by sintering; a material formed by particles attached to one another by a binder; and a monolithic solid in which are defined channels running through said monolithic solid.

8. The system of claim 1, wherein the CX solids are affixed to the porous matrix by a means selected from the group consisting of: formation of covalent, ionic, or hydrogen bonds between CX surface molecules and the matrix; the presence of an adhesive between the solid and a matrix surface; adhesion to a matrix surface by a melt step; partial embedding within the matrix; full embedding within the matrix; and physical retention by fibers within the matrix.

9. The system of claim 1, wherein the system further comprises a material selected from the group consisting of: an adhesive that affixes CX solids to the matrix; a binder that holds CX solid particles in close proximity to one another; a water-insoluble superabsorbent polymer that retains water in close proximity to the CX solids; and an insoluble hygroscopic salt that absorbs water from fluid media and retains the water in close proximity to the CX solids.

10. The system of claim 1, wherein:

a) the system further comprises grains having a composition selected from the group consisting of: a phosphate of calcium; a carbonate of calcium; carbon; and sand; and b) the grains are disposed before, within pores of, embedded in the porous matrix, or after the porous matrix, relative to a flow of fluid during filtration.

11. The system of claim 1, wherein the porous matrix is comprised of:

a) an upstream zone within which the chlorhexidine particles are permanently affixed; and b) a downstream zone that is essentially free of chlorhexidine particles.

12. The system of claim 1, configured for a method of use that comprises, in order:

a) supplying an influent fluid for which antimicrobial treatment or assurance of safety is desired;

b) physically directing the fluid such that said directed fluid passes through the porous matrix and emerges as effluent; and c) directing effluent from the system for storage, immediate use, or further processing.

13. The system of claim 1, configured for a device that comprises, in order:

a) a supply module that provides an influent fluid;

b) a treatment module that receives influent from the supply module, and passes said influent through the porous matrix to emerge as effluent; and c) an exit module that receives treated effluent from the treatment module and channels or delivers said treated effluent for storage, immediate use, or further processing;

wherein the device further comprises a housing.

14. The system of claim 13, wherein the supply module, treatment module, and exit module are inline in a continuous purification process.

15. The system of claim 13, wherein the system is comprised in a configuration for a batch process in the treatment module.

16. The system of claim 13, configured for delivery of purified fluid at the point of use.

17. The system of claim 13, wherein the system is comprised in a unit selected from the group consisting of the following: a water treatment facility for multiple end users; a point-of-use filter on plumbing for potable water; a drinking straw; a feature for purification of a fluid during storage of said fluid; a mask for breathing purified air; a filter for a ventilation system; a showerhead; a vaporizer for medical use; a sports mister for cooling; a filter for a fluid supplied to a fermentation broth; a filter for a bodily fluid; and a filter for a medication-containing fluid.

18. The system of claim 13, wherein the system is comprised in a treatment cartridge for use in a water supply for a residence, office, production facility, hotel, hospital, cruise ship or water treatment plant.

19. The system of claim 13, further comprising a sufficient quantity of a phosphate of calcium to remove at least 50% by weight of a dissolved metal substance from the influent in at least 800 gallons of room-temperature water per cubic inch of foam in a microbicidal filter.

20. The system of claim 13, further comprising a sufficient quantity of a purifying substance to remove from the influent at least 50% by weight of at least one inorganic impurity selected from the group consisting of: trivalent arsenic; pentavalent arsenic; hydrogen sulfide; iron; copper; zinc; lead; aluminum; chromium; uranium; or a combination thereof; for at least 800 gallons of room temperature water per cubic inch of foam in a microbicidal filter.

\* \* \* \* \*